US006740045B2

(12) United States Patent
Amano

(10) Patent No.: US 6,740,045 B2
(45) Date of Patent: May 25, 2004

(54) CENTRAL BLOOD PRESSURE WAVEFORM ESTIMATION DEVICE AND PERIPHERAL BLOOD PRESSURE WAVEFORM DETECTION DEVICE

(75) Inventor: Kazuhiko Amano, Yokohama (JP)

(73) Assignee: Seiko Epson Corporation, Tokyo (JP)

( * ) Notice: Subject to any disclaimer, the term of this patent is extended or adjusted under 35 U.S.C. 154(b) by 127 days.

(21) Appl. No.: 10/123,135

(22) Filed: Apr. 17, 2002

(65) Prior Publication Data

US 2002/0177781 A1 Nov. 28, 2002

(30) Foreign Application Priority Data

Apr. 19, 2001 (JP) ......................................... 2001-121583

(51) Int. Cl.[7] ................................................ A61B 5/02
(52) U.S. Cl. ........................ 600/485; 600/300; 600/501
(58) Field of Search ................................. 600/300–301, 600/485–507

(56) References Cited

U.S. PATENT DOCUMENTS

| 5,033,472 A | * | 7/1991 | Sato et al. ................... 600/504 |
| 5,265,011 A | * | 11/1993 | O'Rourke ................... 600/485 |
| 5,560,366 A | * | 10/1996 | Harada et al. ............... 600/494 |
| 5,564,427 A | * | 10/1996 | Aso et al. ................... 600/494 |
| 5,746,698 A | * | 5/1998 | Bos et al. ................... 600/493 |
| 5,785,659 A | * | 7/1998 | Caro et al. .................. 600/485 |
| 5,836,887 A | * | 11/1998 | Oka et al. ................... 600/494 |
| 5,882,311 A | * | 3/1999 | O'Rourke ................... 600/485 |
| 6,010,457 A | * | 1/2000 | O'Rourke ................... 600/500 |
| 6,254,544 B1 | * | 7/2001 | Hayashi ...................... 600/500 |
| 6,428,482 B1 | * | 8/2002 | Sunagawa et al. .......... 600/485 |
| 6,482,163 B2 | * | 11/2002 | Oka et al. ................... 600/481 |

FOREIGN PATENT DOCUMENTS

| JP | A 10-94526 | 4/1998 |
| JP | A 2000-333910 | 12/2000 |
| JP | A 2000-333911 | 12/2000 |

OTHER PUBLICATIONS

Nichols et al., "McDonald's Blood Flow in Arteries—Theoretical, experimental and clinical principles" (Fourth Edition), Chapter 22.

* cited by examiner

Primary Examiner—Robert L. Nasser
Assistant Examiner—Patricia C Mallari
(74) Attorney, Agent, or Firm—Oliff & Berridge, PLC

(57) ABSTRACT

A central blood pressure waveform estimation device has a pulse wave detection section, a transfer function storage section, and a central blood pressure waveform calculation section. The pulse wave detection section non-invasively detects a peripheral pulse wave. The transfer function storage section stores a transfer function calculated in advance based on a peripheral pulse waveform detected by the pulse wave detection section and a central blood pressure waveform invasively measured. The central blood pressure waveform calculation section calculates a central blood pressure waveform based on a peripheral pulse waveform newly detected by the pulse wave detection section and the transfer function stored in the transfer function storage section.

48 Claims, 14 Drawing Sheets

CENTRAL BLOOD PRESSURE WAVEFORM ESTIMATION DEVICE AND PERIPHERAL BLOOD PRESSURE WAVEFORM DETECTION DEVICE

Japanese Patent Application No. 2001-121583 filed on Apr. 19, 2001, is hereby incorporated by reference in its entirety.

BACKGROUND OF THE INVENTION

The present invention relates to a central blood pressure waveform estimation device and a peripheral blood pressure waveform detection device.

A central blood pressure, specifically, a blood pressure and a blood pressure waveform in the origin of the aorta can be important information for treatment policy planning, post-operative or post-treatment management, intensity management in ergotherapy, and the like for patients suffering from a heart disease. However, it is difficult to non-invasively measure the central blood pressure. In particular, it is very difficult to measure the central blood pressure when the patient takes exercise or the like. Because of this, the central blood pressure and the blood pressure waveform are not generally utilized in clinical applications.

The blood pressure waveform in the peripheral vessel is considered to be the central blood pressure waveform changed by transmission characteristics of a tube through which the pressure wave is transmitted. Based on this idea, it is known in the art that the central blood pressure waveform can be derived from the pressure pulse waveform in the peripheral artery with high precision using a transfer function measured in advance between the blood pressure waveform in the origin of the aorta and the blood pressure waveform in the peripheral artery such as the brachial artery or the radial artery, specifically, the pressure pulse waveform.

It is also known in the art that the pressure pulse wave in the peripheral artery such as the radial artery can be non-invasively detected with high precision using applanation tonometry which measures the pressure using a pressure sensor pressed against the artery so that part of the blood vessel wall is flattened.

Details of these studies are described in *McDonald's Blood Flow in Arteries—Theoretical, Experimental and Clinical Principles* (Fourth Edition), Chapter 22, by W. W. Nichols and M. F. O'Rourke.

However, it is necessary to measure the pulse wave while allowing the person being measured to be in a resting state in order to stably detect the pulse wave in the peripheral artery such as the radial artery using applanation tonometry or the like.

Moreover, since only one transfer function is used to derive the blood pressure waveform in the aorta from the pulse wave in the peripheral artery regardless of the age and state of the subject, it may be difficult to maintain precision of the blood pressure waveform in the aorta to be derived.

BRIEF SUMMARY OF THE INVENTION

The present invention has been achieved in view of the above-described problems. The present invention may provide a central blood pressure waveform estimation device exhibiting at least one of the following effects.

(1) A central blood pressure waveform can be derived by using a waveform of a peripheral pulse wave which is non-invasively detected.

(2) A pulse wave in a peripheral artery can be stably detected without forcing a subject to be in a resting state.

(3) A central blood pressure waveform can be derived from a pulse wave in a peripheral artery with high precision regardless of an age or state of an subject.

A central blood pressure waveform estimation device according to a first aspect of the present invention comprises:

a pulse wave detection section which non-invasively detects a peripheral pulse wave;

a transfer function storage section which stores a transfer function calculated in advance based on a waveform of the peripheral pulse wave detected by the pulse wave detection section and a central blood pressure waveform corresponding to the peripheral pulse waveform; and a central blood pressure waveform calculation section which calculates a central blood pressure waveform corresponding to a waveform of a peripheral pulse wave newly detected by the pulse wave detection section, based on the newly-detected peripheral pulse waveform and the transfer function.

According to the first aspect of the present invention, a central blood pressure waveform, specifically, a blood pressure waveform in an origin of an aorta can be derived from a peripheral pulse waveform which is non-invasively detected.

A central blood pressure waveform estimation device according to a second aspect of the present invention comprises:

a pulse wave detection section which non-invasively detects a peripheral pulse wave;

a transfer function storage section which stores a transfer function calculated in advance based on a waveform of the peripheral pulse wave detected previously and a central blood pressure waveform corresponding to the peripheral pulse waveform; and a central blood pressure waveform calculation section which calculates a central blood pressure waveform corresponding to a waveform of a peripheral pulse wave newly detected by the pulse wave detection section, based on the newly-detected peripheral pulse waveform and the transfer function.

"A waveform of the peripheral pulse wave detected previously" is a waveform of a peripheral pulse wave detected by a device for pulse wave detection formed in the same manner as the above pulse wave detection section, for example.

According to the second aspect of the present invention, a blood pressure waveform in an aorta can be derived from a peripheral pulse waveform which is non-invasively detected.

Moreover, since a transfer function calculated in advance based on a waveform of a peripheral pulse wave detected by a device for pulse wave detection formed in the same manner as the pulse wave detection section of the central blood pressure waveform estimation device is stored in the transfer function storage section, it is unnecessary to calculate a transfer function for each central blood pressure waveform estimation device.

A central blood pressure waveform estimation device according to a third aspect of the present invention comprises:

a pulse wave detection section which non-invasively detects a peripheral pulse wave;

a blood pressure measurement section which measures a blood pressure in an area near a portion in which a peripheral pulse wave is detected by the pulse wave detection section;

a conversion section which converts a waveform of the peripheral pulse wave detected by the pulse wave detection section into a peripheral blood pressure waveform using a value of the blood pressure measured by the blood pressure measurement section;

a transfer function storage section which stores a transfer function calculated in advance based on the peripheral blood pressure waveform obtained by the conversion section and a central blood pressure waveform corresponding to the peripheral blood pressure waveform; and a central blood pressure waveform calculation section which calculates a central blood pressure waveform corresponding to a peripheral blood pressure waveform obtained by converting a waveform of a pulse wave newly detected by the pulse wave detection section using the conversion section, based on this peripheral blood pressure waveform and the transfer function.

According to the third aspect of the present invention, a blood pressure waveform in an aorta can be derived from a peripheral blood pressure waveform obtained by converting a waveform of a peripheral pulse wave which is non-invasively detected.

A central blood pressure waveform estimation device according to a fourth aspect of the present invention comprises:

a pulse wave detection section which non-invasively detects a peripheral pulse wave;

a blood pressure value storage section which stores a value of a blood pressure measured previously in an area near a portion in which a peripheral pulse wave is detected by the pulse wave detection section;

a conversion section which converts a waveform of the peripheral pulse wave detected by the pulse wave detection section into a peripheral blood pressure waveform using the blood pressure value stored in the blood pressure value storage section;

a transfer function storage section which stores a transfer function calculated in advance based on the peripheral blood pressure waveform obtained by the conversion section and a central blood pressure waveform corresponding to the peripheral blood pressure waveform; and a central blood pressure waveform calculation section which calculates a central blood pressure waveform corresponding to a peripheral blood pressure waveform obtained by converting a waveform of a pulse wave newly detected by the pulse wave detection section using the conversion section, based on the peripheral blood pressure waveform and the transfer function.

According to the fourth aspect of the present invention, a blood pressure waveform in an aorta can be derived from a waveform of a peripheral pulse wave which is non-invasively detected using the blood pressure value storage section in place of the blood pressure measurement section according to the third aspect of the invention.

Each of the central blood pressure waveform estimation devices according to the first to fourth aspects of the present invention may further comprise a central blood pressure waveform index derivation section which derives an index from a central blood pressure waveform calculated by the central blood pressure waveform calculation section.

The index derived by the central blood pressure waveform index derivation section may be a pre-systolic blood pressure.

The index derived by the central blood pressure waveform index derivation section maybe a post-systolic blood pressure.

The index derived by the central blood pressure waveform index derivation section may be a diastolic blood pressure.

The index derived by the central blood pressure waveform index derivation section may be a differential pressure between a post-systolic blood pressure and a blood pressure at a dicrotic notch.

The index derived by the central blood pressure waveform index derivation section may be a ratio of a post-systolic blood pressure to a blood pressure at the peak of a tidal wave.

The central blood pressure waveform estimation device having the central blood pressure waveform index derivation section may further comprise:

a central blood pressure waveform index storage section which stores the index of a central blood pressure waveform; and a change analysis section which analyzes the change in the index of a central blood pressure waveform, based on an index newly derived by the central blood pressure waveform index derivation section and the index of the central blood pressure waveform stored in the central blood pressure waveform index storage section.

The change analysis section may include:

a basal central blood pressure waveform index derivation section which derives an index of a basal central blood pressure waveform, which is an index of a central blood pressure waveform when basal metabolism of a subject is in the lowest region in a predetermined period of time, from the index of the central blood pressure waveform stored in the central blood pressure waveform index storage section; and a basal central blood pressure waveform index storage section which stores the basal central blood pressure waveform index derived by the basal central blood pressure waveform index derivation section, wherein the change in the index of a central blood pressure waveform may be analyzed, based on the index of the central blood pressure waveform derived by the central blood pressure waveform index derivation section and the basal central blood pressure waveform index stored in the basal central blood pressure waveform index storage section.

The central blood pressure waveform estimation device having the central blood pressure waveform index derivation section may further comprise:

a data input section to which an actual age of a subject is input; and a comparative analysis section which compares and analyzes an index of a central blood pressure waveform, based on the index of the central blood pressure waveform derived by the central blood pressure waveform index derivation section and a standard index of a central blood pressure waveform at the actual age.

In each of the central blood pressure waveform estimation devices according to the first to fourth aspects of the present invention, the pulse wave detection section may be formed to detect a plethysmogram which changes corresponding to the blood flow, as the change in the amount of erythrocytes in capillary vessels near the skin.

This enables a pulse wave in a peripheral artery to be stably detected without forcing a subject to be in a resting state.

The plethysmogram which changes corresponding to the blood flow can be detected as the change in the amount of erythrocytes in capillary vessels near the skin. Since the change can be detected as a change in the amount of transmission or reflection of light irradiated onto the skin, it is not necessary to place a sensor at a position of a peripheral artery such as a radial artery. Because of this, the pulse wave detection section can stably detect the change in the amount of erythrocytes in capillary blood vessels near the skin as a pulse wave in the peripheral artery (plethysmogram).

In each of the central blood pressure waveform estimation devices according to the first to fourth aspects of the present invention, the transfer function storage section may store a plurality of transfer functions corresponding to a plurality of different states of a single subject such as states in which at least one of a cardiac function state and an arterial state differs. The transfer function is not constant for a single subject. The transfer function is changed depending upon the cardiac function state, arterial state, psychological tension state, psychological relaxation state, or the like. Since the state of an subject whose central blood pressure waveform is estimated by measuring the pulse wave varies at the time of measurement, the transfer functions are stored corresponding to various states. In this case, the central blood pressure waveform calculation section may calculate a central blood pressure waveform by selecting one transfer function corresponding to the pulse rate derived from the pulse wave, for example, from among a plurality of transfer functions based on information detected by the pulse wave detection section.

This enables a central blood pressure waveform to be derived from a pulse wave in a peripheral artery with high precision regardless of a state of a subject.

In each of the central blood pressure waveform estimation devices according to the first to fourth aspects of the present invention, the transfer function storage section may store a plurality of transfer functions corresponding to different ages; and the central blood pressure waveform calculation section may calculate a central blood pressure waveform by selecting a transfer function corresponding to the age of a subject whose pulse wave is detected by the pulse wave detection section, from the plurality of transfer functions.

This enables a central blood pressure waveform to be derived from a pulse wave in a peripheral artery with high precision regardless of the age of a subject.

In each of the central blood pressure waveform estimation devices according to the first to fourth aspects of the present invention, the transfer function storage section may store a plurality of transfer functions corresponding to different physiological ages; and the central blood pressure waveform calculation section may calculate a central blood pressure waveform by selecting a transfer function corresponding to the physiological age of a subject whose pulse wave is detected by the pulse wave detection section from the plurality of transfer functions.

This enables a central blood pressure waveform to be derived from a pulse wave in a peripheral artery with high precision regardless of the physiological age of a subject.

In the central blood pressure waveform estimation device according to the fourth aspect of the present invention, the blood pressure value storage section may store a plurality of blood pressure values corresponding to a plurality of different states of a single subject such as states in which at least one of the cardiac function state and the arterial state differs. In this case, the conversion section may read a blood pressure value selected from the plurality of blood pressure values stored in the blood pressure value storage section, based on information from the pulse wave detection section.

The blood pressure value is not constant for a single subject. The blood pressure value is changed depending upon the cardiac function state, arterial state, psychological tension state, psychological relaxation state, or the like. Since a state of a subject whose central blood pressure waveform is estimated by measuring the pulse wave varies at the time of measurement, the blood pressure values are stored corresponding to various states. Since these various states correlate with heart rate (or pulse rate) or an index which indicates the characteristics of the pulse waveform, the blood pressure values in various states may be connected with heart rate or the above index and stored. In this case, the conversion section may calculate heart rate or the above index or the like based on the information from the pulse wave detection section, and read the blood pressure value selected from a plurality of blood pressure values based on the heart rate or the above index or the like.

Alternatively, states of a subject at the time of measurement may be input. As a state of a subject which may vary the blood pressure value, there are states after a meal, bath, exercise and the like, being different from the resting period, or a psychological tension state or a psychological relaxation state. In addition to the blood pressure value during the resting period, a plurality of blood pressure values corresponding to the above-described states may be stored in the blood pressure value storage section. The conversion section may read a blood pressure value selected from the plurality of blood pressure values based on information from a data input section.

A peripheral blood pressure waveform detection device according to a fifth aspect of the present invention comprises:

a pulse wave detection section which non-invasively detects a peripheral pulse wave;

a blood pressure measurement section which measures a blood pressure in an area near a portion in which a peripheral pulse wave is detected by the pulse wave detection section; and a conversion section which converts a waveform of the peripheral pulse wave detected by the pulse wave detection section into a peripheral blood pressure waveform using a value of the blood pressure measured by the blood pressure measurement section.

A peripheral blood pressure waveform detection device according to a sixth aspect of the present invention comprises:

a pulse wave detection section which non-invasively detects a peripheral pulse wave;

a blood pressure value storage section which stores a value of a blood pressure measured previously in an area near a portion in which a peripheral pulse wave is detected by the pulse wave detection section; and a conversion section which converts a waveform of the peripheral pulse wave detected by the pulse wave detection section into a peripheral blood pressure waveform using the blood pressure value stored in the blood pressure value storage section.

In each of the peripheral blood pressure waveform detection devices according to the fifth and sixth aspects of the present invention, the pulse wave detected by the pulse wave detection section may be a plethysmogram which changes corresponding to the blood flow.

In the peripheral blood pressure waveform detection device according to the sixth embodiment of the present invention, the blood pressure value storage section may store a plurality of blood pressure values corresponding to a plurality of different states of a single subject such as a state in which at least one of the cardiac function state and the arterial state differs.

DETAILED DESCRIPTION OF THE EMBODIMENT

Preferred embodiments of the present invention are described below in detail with reference to the drawings.

Figure 1A:
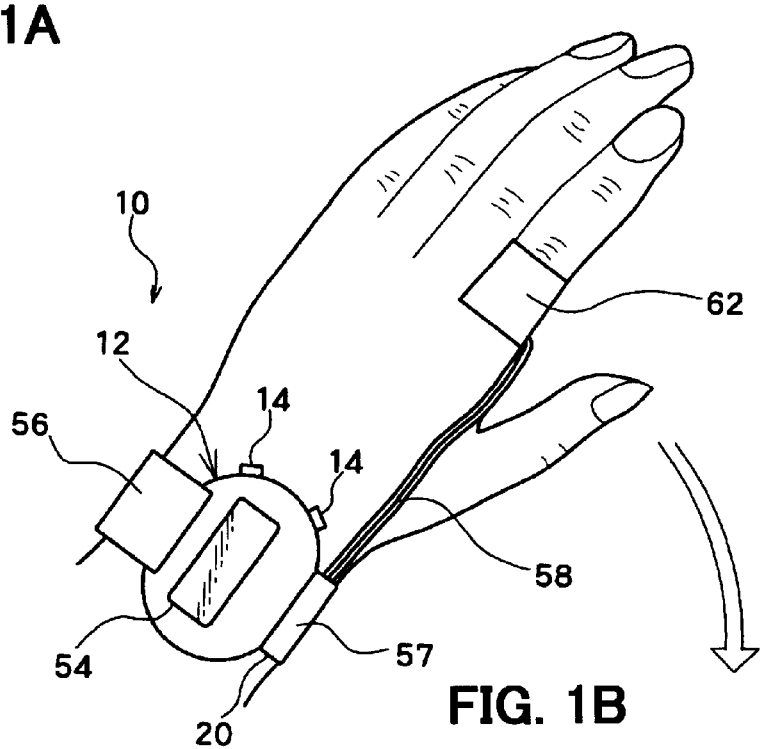
FIGS. 1A, 1B, and 1C are views showing the appearance of a central blood pressure waveform estimation device according to a first embodiment of the present invention.
Figure 1B:
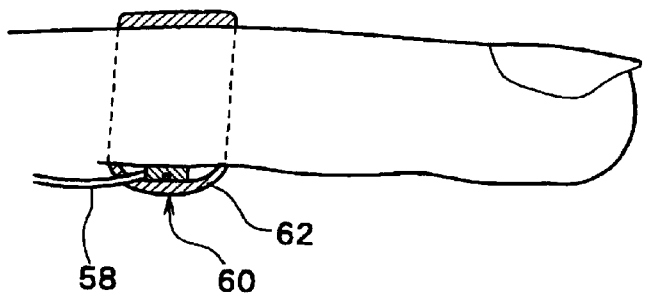
Figure 1C:
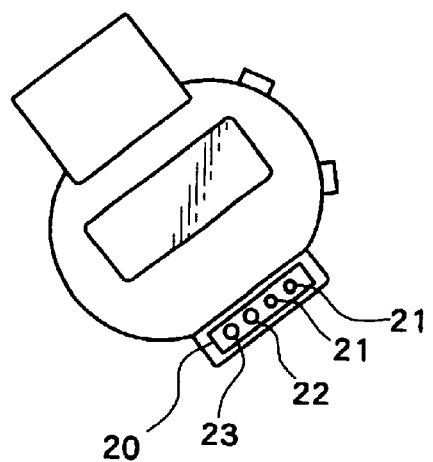

1. First Embodiment 1.1 External Configuration of Central Blood Pressure Waveform Estimation Device A central blood pressure waveform estimation device of the present embodiment may have an external configuration as shown in FIGS. 1A, 1B, and 1C, for example. A central blood pressure waveform estimation device 10 includes a body 12 having a structure in the shape of a wristwatch, a cable 58 connected to a connector section 20 of the body 12 through a connector piece 57, and a pulse wave detection section 60 provided at the end of the cable 58. A wrist band 56 is attached to the body 12. The body 12 is installed on the wrist of a subject using the wrist band 56.

The body 12 includes the connector section 20. The connector piece 57, which is the end of the cable 58, is removably provided to the connector section 20.

FIG. 1C shows the connector section 20 from which the connector piece 57 is removed. The connector section 20 includes connection pins 21 for connecting with the cable 58, an LED 22 and a phototransistor 23 for transferring data, and the like.

A display section 54 including a liquid crystal panel is formed on the surface side of the body 12. The display section 54 has a segment display region, a dot display region, and the like, and displays the central blood pressure waveform, index of the central blood pressure waveform, analysis results, or the like. A display device other than the liquid crystal panel may be used for the display section 54.

The body 12 includes a CPU (central processing unit) which controls various types of operations, conversions, and the like, and a memory in which a program for operating the CPU and the like is stored (not shown). Button switches 14 for performing various types of operations and input are provided on the periphery of the body 12.

The pulse wave detection section 60 is installed near the root of the forefinger of the subject while being shaded by a sensor securing band 62, as shown in FIG. 1B. Since the length of the cable 58 can be decreased by installing the pulse wave detection section 60 near the root of the finger, the subject is not disturbed by the cable 58. Moreover, since the change in the blood flow due to temperature is small near the root of the finger in comparison with the fingertip, the pulse waveform to be detected is less affected by temperature or the like.

Figure 2:
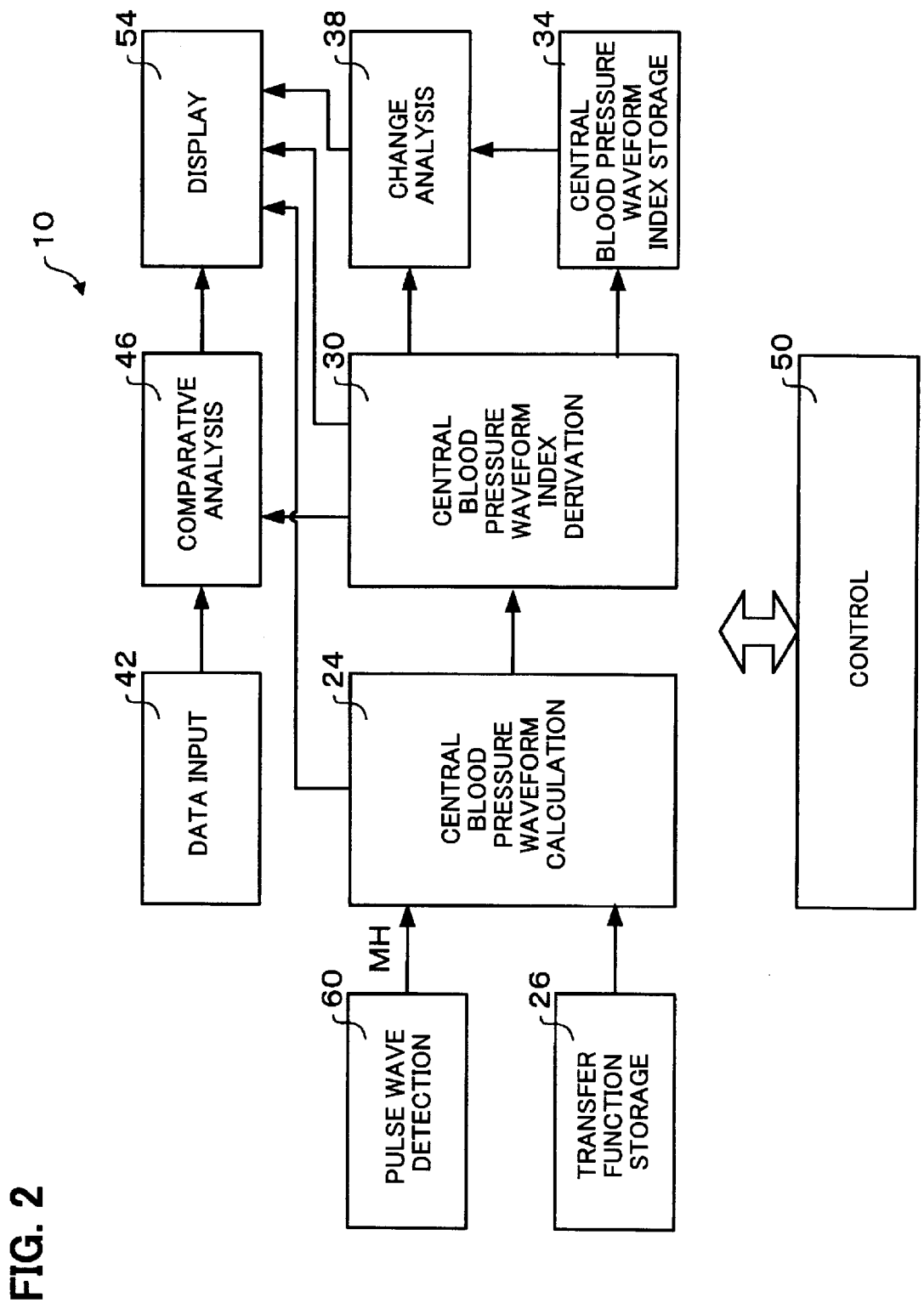
FIG. 2 is a block diagram showing the functional configuration of the central blood pressure waveform estimation device according to the first embodiment of the present invention.

1.2 Functional Configuration of Central Blood Pressure Waveform Estimation Device FIG. 2 is a block diagram showing the functional configuration of the central blood pressure waveform estimation device 10 according to the present embodiment. As shown in FIG. 2, the central blood pressure waveform estimation device 10 includes the pulse wave detection section 60, transfer function storage section 26, central blood pressure waveform calculation section 24, central blood pressure waveform index calculation section 30, data input section 42, comparative analysis section 46, central blood pressure waveform index storage section 34, change analysis section 38, display section 54, and control section 50. Each of these sections may be incorporated in the body 12, or individually formed and electrically connected with the pulse wave detection section 60, display section 54, or the like.

Figure 3:
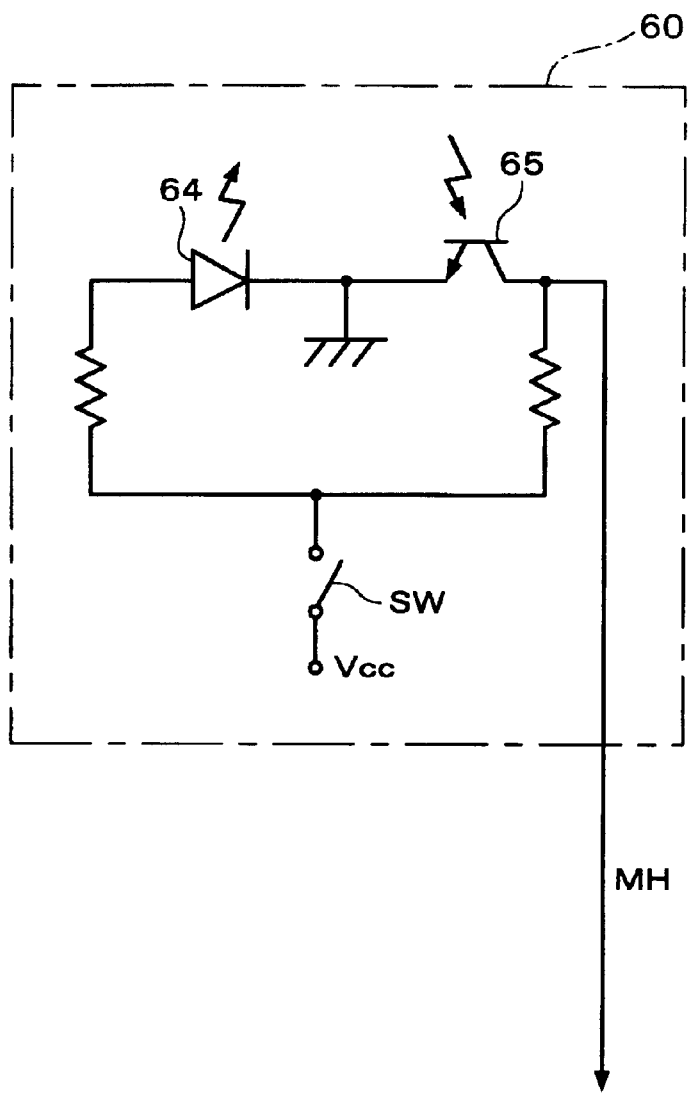
FIG. 3 is a circuit diagram showing an example of the circuit configuration of the pulse wave detection section.

As shown in FIG. 3, the pulse wave detection section 60 includes an LED 64, a phototransistor 65, and the like so that the peripheral pulse wave can be detected non-invasively, specifically, without breaking the skin. The pulse wave detection section 60 utilizes a phenomenon in which the pulse waveform is almost similar to the waveform of the change in the blood flow (plethysmogram waveform) to detect the pulse wave (plethysmogram) using a photosensor formed to emit light to the capillary plexus and detect the change in the amount of reflected light or transmitted light due to blood in the capillary blood vessels.

More specifically, when a switch SW is turned ON, a power supply voltage is applied to the pulse wave detection section 60, whereby light is emitted from the LED 64. The emitted light is reflected by the blood vessel or tissue of the subject, and received by the phototransistor 65. Therefore, a photocurrent of the phototransistor 65 converted into a voltage is output as a signal MH of the pulse wave detection section 60.

The emission wavelength of the LED 64 is selected near the peak of the absorption wavelength of the hemoglobin in blood. Therefore, the light receiving level is changed corresponding to the blood flow. Because of this, the pulse waveform is detected by detecting the light receiving level. As the LED 64, a blue InGaN (indium-gallium-nitrogen) LED is preferable. The emission spectrum of the LED may have an emission peak of about 450 nm and an emission wavelength region ranging from 350 to 600 nm.

As the phototransistor 65 corresponding to the LED having such emission characteristics, a GaAsP (gallium-arsenic-phosphorus) phototransistor may be used in the present embodiment. The phototransistor 65 may have a main sensitivity region at 300 to 600 nm and also have a sensitivity region at 300 nm or less.

Since the pulse wave can be detected in the wavelength region of 300 to 600 nm by combining the blue LED 64 with the phototransistor 65, the following advantages can be obtained.

Light having a wavelength region of 700 nm or less contained in external light is transmitted through the tissue of the finger to only a small extent. Therefore, even if the external light is irradiated to the finger in the area in which the finger is not covered with the sensor securing band, the external light does not reach the phototransistor 65 through the tissue of the finger. Only light having a wavelength region which does not affect the detection of the pulse wave reaches the phototransistor 65. Light having a wavelength region longer than 300 nm is almost completely absorbed on the surface of the skin. Therefore, if the light receiving wavelength region is set to 700 nm or less, the substantial light receiving wavelength region is 300 to 700 nm. As a result, effects caused by external light can be limited without covering the finger over a wide range. Moreover, hemoglobin in blood has a large absorption coefficient for light having a wavelength of 300 to 700 nm, which is from several to about one hundred times or more greater than the absorption coefficient for light having a wavelength of 880 nm. Therefore, in the case where light having a wavelength region (300 to 700 nm) with large absorption characteristics is used as the light for detection corresponding to the absorption characteristics of the hemoglobin as in this example, the detected value is changed corresponding to the change in the blood flow with high sensitivity, whereby the SN ratio of the pulse waveform MH based on the change in the blood flow can be increased.

Since the pulse wave detection section 60 can detect the pulse wave which is changed corresponding to the blood flow (plethysmogram) as the change in the transmission or reflection amount of light irradiated to the skin (change in the amount of erythrocytes in the capillary plexus present near the skin), the pulse wave can be detected without placing the sensor at a position of a peripheral artery such as the radial artery or digital artery. Because of this, the pulse wave detection section 60 can stably detect the change in the amount of erythrocytes in the capillary blood vessels present near the skin as the pulse wave in the peripheral artery (plethysmogram).

Figure 4A:
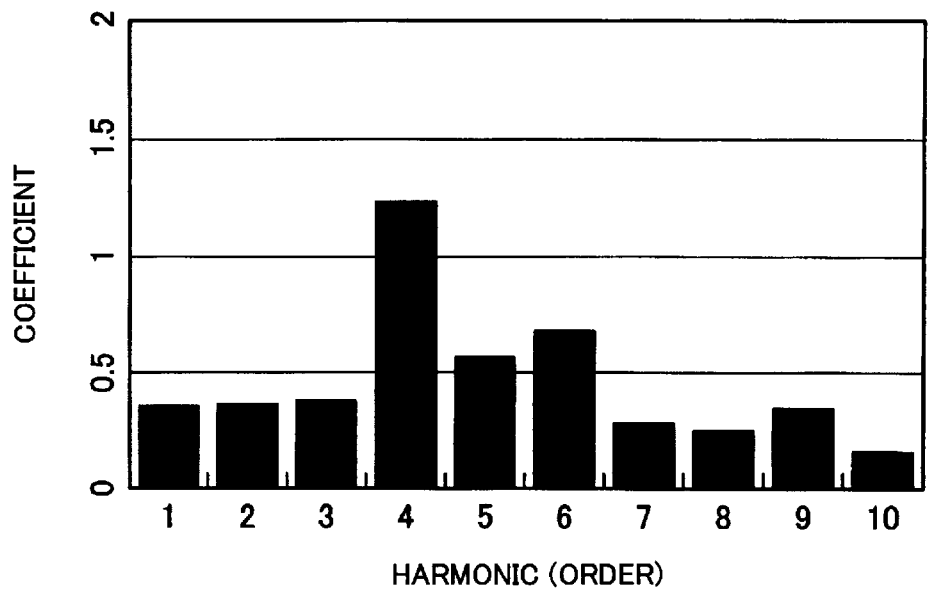
FIGS. 4A and 4B are bar charts of a coefficient and a phase for each harmonic, showing examples of a transfer function stored in the transfer function storage section.
Figure 4B:
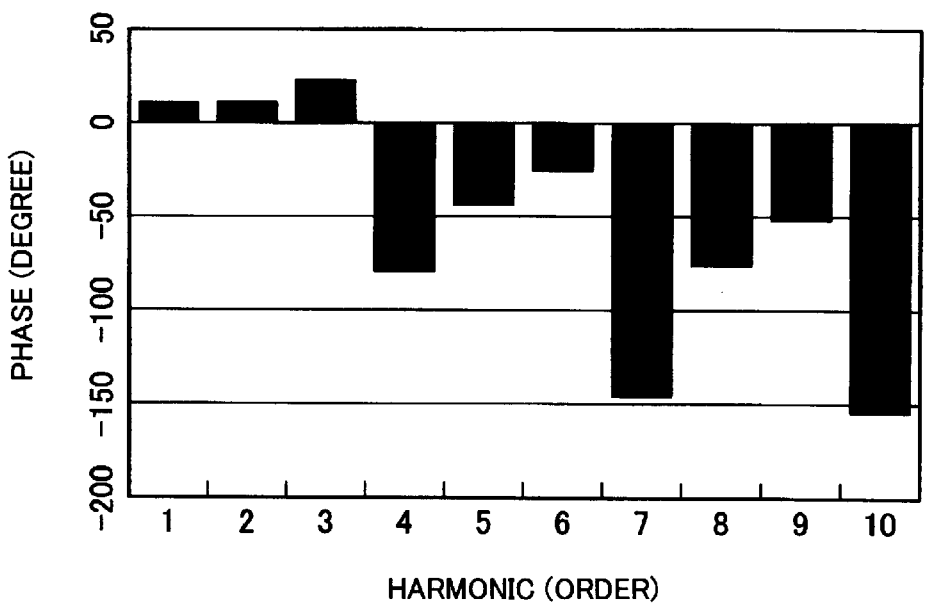

The transfer function storage section 26 stores the transfer function calculated in advance based on the central blood pressure waveform (blood pressure waveform in the origin of the aorta) measured using a micro-manometer utilizing a catheter or the like and the peripheral pulse waveform detected in advance by the pulse wave detection section 60. FIGS. 4A and 4B show examples of the transfer function as graphs of the coefficient and the phase for each harmonic.

The transfer function storage section 26 may store the transfer function calculated in advance based on the pulse waveform detected in advance by a pulse wave detection section formed in the same manner as the pulse wave detection section 60, and the central blood pressure waveform invasively measured in advance. It is known that there is only a small difference in the transfer function between each individual. Therefore, a commonly applicable general-purpose transfer function may be used.

The central blood pressure waveform calculation section 24 calculates the central blood pressure waveform using the transfer function stored in the transfer function storage section 26 and the peripheral pulse waveform detected by the pulse wave detection section 60 corresponding to this pulse waveform. For example, the central blood pressure waveform calculation section 24 calculates the central blood pressure waveform by Fourier transforming the peripheral pulse waveform detected by the pulse wave detection section 60, dividing the transformed waveform by the transfer function stored in the transfer function storage section 26, and inverse Fourier transforming the results.

The central blood pressure waveform index derivation section 30 derives the index of the central blood pressure waveform from the central blood pressure waveform calculated by the central blood pressure waveform calculation section 24. The central blood pressure waveform index derivation section 30 outputs the derived index of the central blood pressure waveform to the central blood pressure waveform index storage section 34, the change analysis section 38, the comparative analysis section 46, and the display section 54. The central blood pressure waveform index derivation section 30 includes a CPU and a memory in which a program for operating the CPU is stored, for example.

Figure 5:
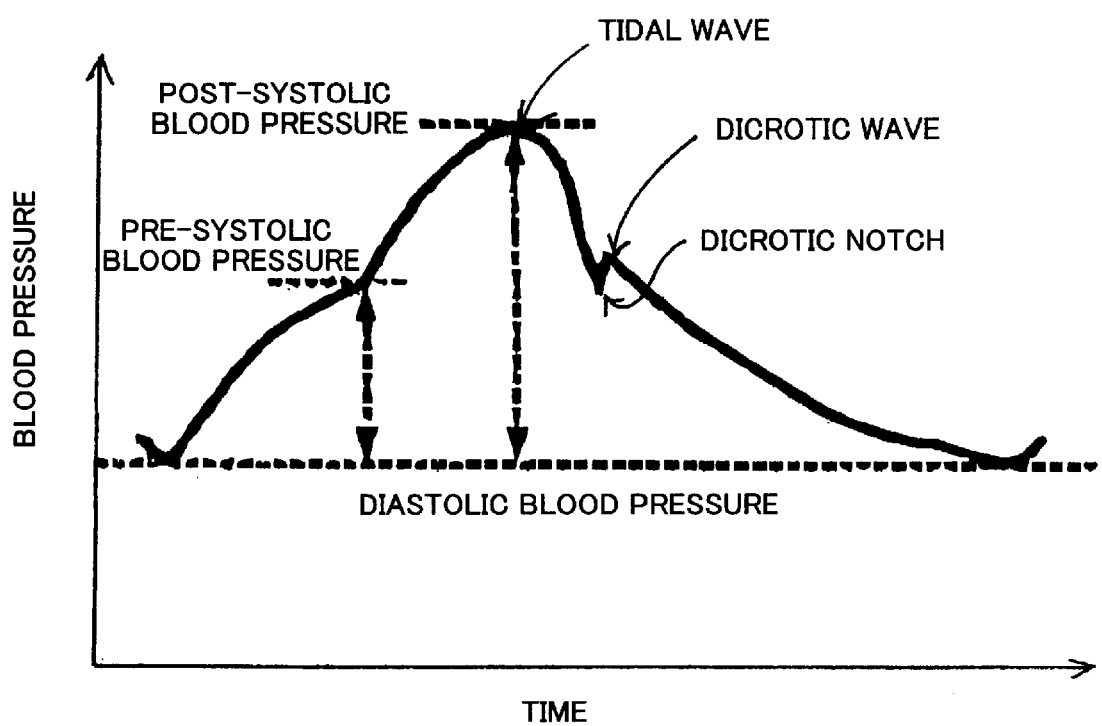
FIG. 5 is a graph showing a typical central blood pressure waveform.

The central blood pressure waveform is described below with reference to FIG. 5. FIG. 5 shows a typical central blood pressure waveform, specifically, the blood pressure waveform in the origin of the aorta. As shown in FIG. 5, the features of the central blood pressure waveform may be referred to as a pre-systolic blood pressure, post-systolic blood pressure, tidal wave, dicrotic notch, dicrotic wave, and the like.

The central blood pressure waveform index derivation section 30 derives the differential pressure between the post-systolic blood pressure and the blood pressure at the dicrotic notch, the ratio of the post-systolic blood pressure to the blood pressure at the peak of the tidal wave, the pre-systolic blood pressure, the post-systolic blood pressure, or the diastolic blood pressure as an index from the central blood pressure waveform.

The data input section 42 is formed so that the subject's actual age is input by the operation of the button switches 14 or using a voice command entered through a microphone (not shown), for example. The data input section 42 outputs the actual age to the comparative analysis section 46 as data.

The comparative analysis section 46 stores standard values for the differential pressure between the systolic blood pressure and the blood pressure at the dicrotic notch and the ratio of the systolic blood pressure to the blood pressure at the peak of the tidal wave corresponding to each age. The comparative analysis section 46 compares the index of the central blood pressure output from the central blood pressure waveform index derivation section 30 with the standard index value of the actual age of the subject input to the data input section 42, and analyzes the results, for example. The comparative analysis section 46 outputs the difference therebetween to the display section 54. The comparative analysis section 46 includes a CPU and a memory in which a program for operating the CPU is stored.

The central blood pressure waveform index storage section 34 includes a semiconductor memory, or a storage medium utilizing magnetism or light and a semiconductor memory in combination. The central blood pressure waveform index storage section 34 stores the index output from the central blood pressure waveform index derivation section 30 for at least a predetermined period of time.

The change analysis section 38 analyzes the change in the index based on the index derived by the central blood pressure waveform index derivation section 30 and the index stored in the central blood pressure waveform index storage section 34, and calculates the amount of change, changing rate, and the like. The analysis results are output to the display section 54.

The display section 54 displays information such as the index derived by the central blood pressure waveform index derivation section 30, analysis results by the comparative analysis section, analysis results by the change analysis section 38, or central blood pressure waveform (blood pressure waveform in the origin of the aorta) calculated using the central blood pressure waveform calculation section 24, using characters, symbols, graphs, or the like.

The control section 50 includes a CPU and a memory in which a program for operating the CPU is stored, and controls the operations of each of the above-described sections.

1.3 Operation of Central Blood Pressure Waveform Estimation Device

The central blood pressure waveform estimation device 10 operates as follows to estimate and analyze the central blood pressure waveform of the subject, for example.

The wrist band 56 of the central blood pressure waveform estimation device 10 formed in the shape of a watch is wound around the wrist. The pulse wave detection section 60 is installed near the root of the forefinger of the subject, as shown in FIGS. 1A and 1B. The pulse wave detection section 60 is connected with the body 12 by attaching the connector piece 57 to the connector section 20 of the body 12.

The actual age of the subject is input to the data input section 42 which includes the button switches 14, or is formed to allow a voice command to be input through a microphone, by operating the button switches 14 or inputting the voice command. The data is stored in the comparative analysis section 46.

When the detection instruction is input to the control section 50 by a predetermined operation of the button switches 14 or using a predetermined voice pattern, the pulse wave detection section 60 starts to detect the pulse wave. Specifically, when the detection instruction is input, the phototransistor 65 detects the amount of light changed corresponding to the change in the blood flow in the capillary plexus of the finger. The pulse wave detection section 60 outputs the pulse waveform as the signal MH corresponding to the change in the detected amount of light to the central blood pressure waveform calculation section 24.

The central blood pressure waveform calculation section 24 calculates the central blood pressure waveform using the pulse waveform input from the pulse wave detection section 60 and the transfer function stored in the transfer function storage section 26 corresponding to this pulse waveform. The calculated central blood pressure waveform is output to the central blood pressure waveform index calculation section 30 and the display section 54.

The central blood pressure waveform index derivation section 30, to which the central blood pressure waveform calculated by the central blood pressure waveform calculation section 24 is input, derives the index of the central blood pressure waveform such as the differential pressure between the systolic blood pressure and the blood pressure at the dicrotic notch or the ratio of the systolic blood pressure to the blood pressure at the peak of the tidal wave from the central blood pressure waveform. The central blood pressure waveform index derivation section 30 outputs the derived index of the central blood pressure waveform to the central blood pressure waveform index storage section 34, the change analysis section 38, the comparative analysis section 46, and the display section 54. The change analysis section 38 and the comparative analysis section 46 perform analysis using the input index.

The display section 54 including a liquid crystal display device or the like displays the central blood pressure waveform calculated by the central blood pressure waveform calculation section 24, the index derived by the central blood pressure waveform index derivation section 30, or analysis results by the comparative analysis section 46 or change analysis section 38, using characters, graphs, or the like.

1.4 Effects of First Embodiment

As described above, the central blood pressure waveform estimation device 10 according to the present embodiment is capable of deriving the central blood pressure waveform (blood pressure waveform in the origin of the aorta) using the peripheral pulse waveform which is non-invasively detected.

2. Second Embodiment

A central blood pressure waveform estimation device of the second embodiment differs from the central blood pressure waveform estimation device of the first embodiment in that a blood pressure measurement section and a conversion section are provided. In the following description, features differing from the first embodiment are mainly described. Since other features are the same as in the first embodiment, description thereof is omitted. In the figures, corresponding sections are indicated by the same symbols.

2.1 External Configuration of Central Blood Pressure Waveform Estimation Device

The central blood pressure waveform estimation device of the present embodiment has an external configuration consisting of sections formed almost in the same external shape as the central blood pressure waveform estimation device 10 of the first embodiment and a section of the blood pressure measurement section.

Figure 6:
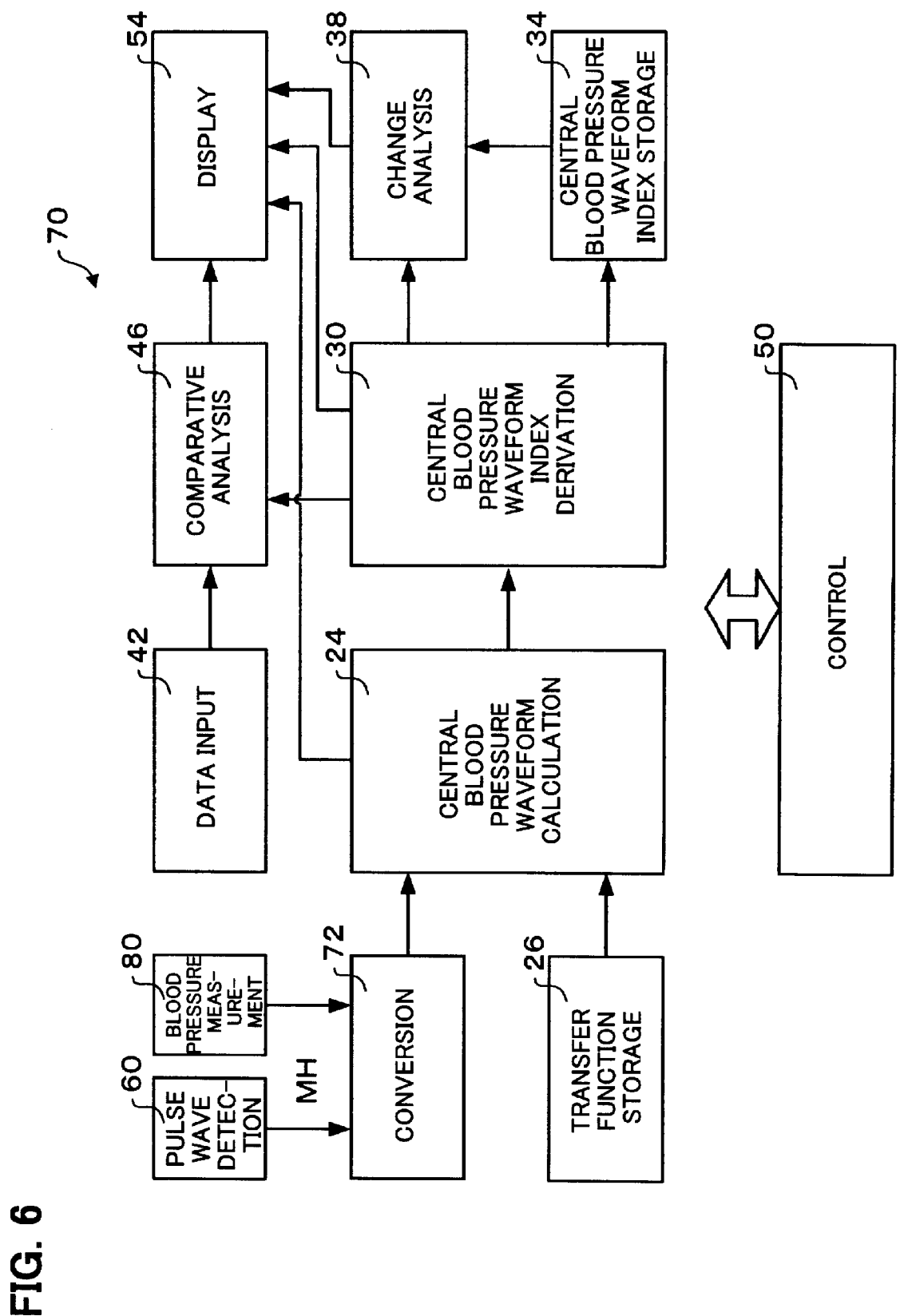
FIG. 6 is a block diagram showing the functional configuration of a central blood pressure waveform estimation device according to a second embodiment of the present invention.

2.2 Functional Configuration of Central Blood Pressure Waveform Estimation Device FIG. 6 is a block diagram showing the functional configuration of a central blood pressure waveform estimation device 70 according to the present embodiment. As shown in FIG. 6, the central blood pressure waveform estimation device 70 includes a blood pressure measurement section 80 and a conversion section 72 in addition to each section of the central blood pressure waveform estimation device 10 of the first embodiment. Each section of the central blood pressure waveform estimation device 70 according to the present embodiment is the same as those of the central blood pressure waveform estimation device 10 of the first embodiment excluding the blood pressure measurement section 80 and the conversion section 72.

The blood pressure measurement section 80 measures the blood pressure in the area in which the pulse wave detection section 60 detects the pulse wave. An example of the blood pressure measurement section 80 is described later.

The conversion section 72 converts the pulse waveform detected by the pulse wave detection section 60 into the blood pressure waveform in the area in which the pulse waveform is detected, specifically, the peripheral blood pressure waveform using the blood pressure value measured by the blood pressure measurement section 80. For example, the conversion section 72 converts the pulse waveform into the corresponding blood pressure waveform by allowing the pulse waveform to have an amplitude between the diastolic blood pressure and the post-systolic blood pressure measured by the blood pressure measurement section.

Figure 13:
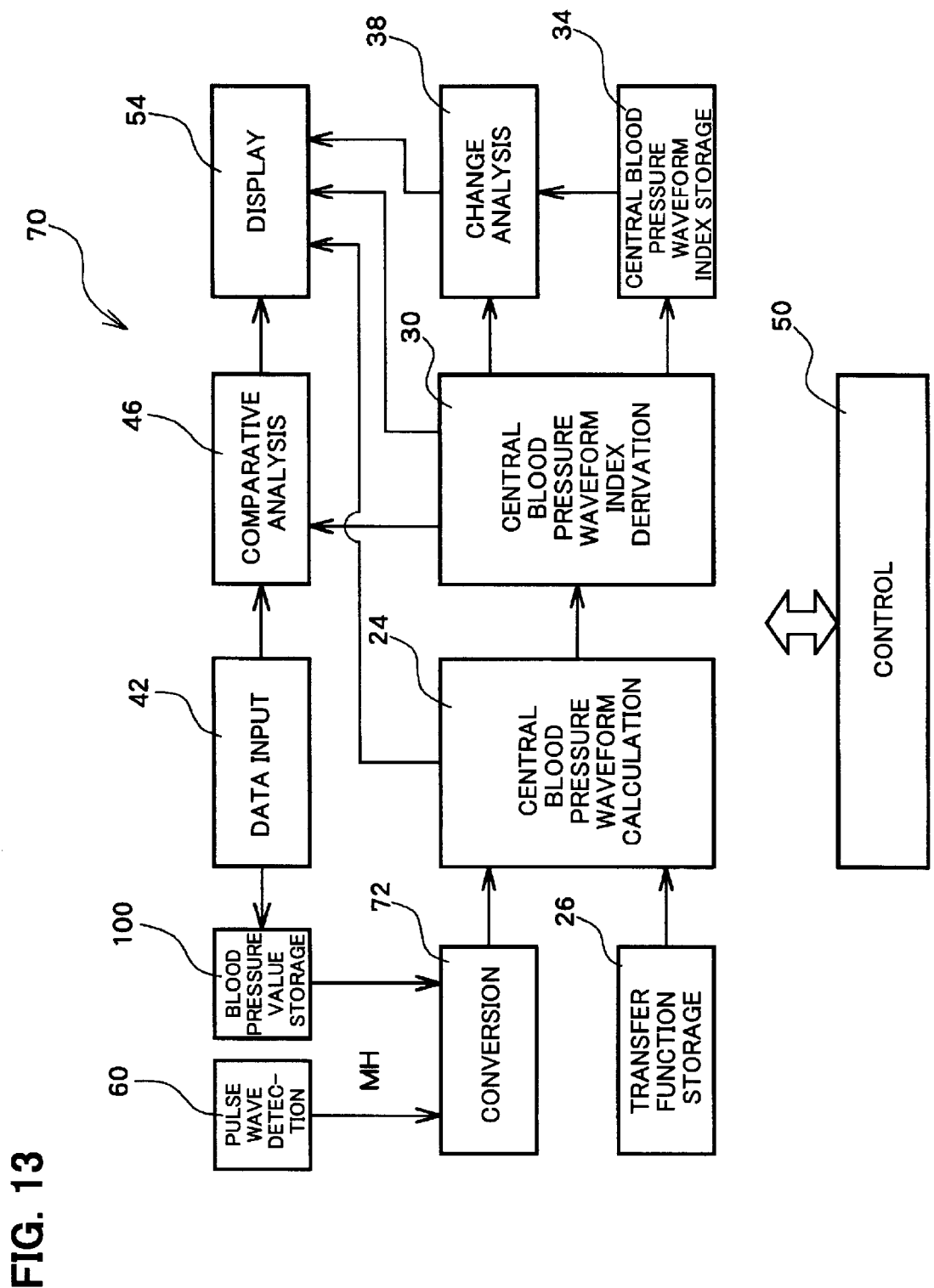
FIG. 13 is a block diagram showing a central blood pressure waveform estimation device according to another embodiment of the present invention, in which a blood pressure value storage section is provided in place of the blood pressure measurement section shown in FIG. 6.

As shown in FIG. 13, a blood pressure value storage section 100 may be provided in place of the blood pressure measurement section 80 shown in FIG. 6. The blood pressure value storage section 100 stores the blood pressure value measured in advance in the area in which the pulse wave detection section 60 detects the pulse wave. The conversion section 72 may convert the pulse waveform detected by the pulse wave detection section 60 into the peripheral blood pressure waveform using the blood pressure value stored in the blood pressure value storage section 100. This eliminates the need for the blood pressure measurement section 80 once the blood pressure is measured using the blood pressure measurement section 80 shown in FIG. 7 and stored in the blood pressure value storage section 100, for example. As a result, the size of the device can be significantly decreased.

The central blood pressure waveform calculation section 24 calculates the central blood pressure waveform using the transfer function stored in the transfer function storage section 26 and the blood pressure waveform calculated by the conversion section 72 corresponding to this blood pressure pulse waveform. For example, the central blood pressure waveform calculation section 24 calculates the central blood pressure waveform by Fourier transforming the peripheral blood pressure waveform calculated by the conversion section 72, dividing the transformed waveform by the transfer function stored in the transfer function storage section 26, and inverse Fourier transforming the results.

2.3 Blood Pressure Measurement Section

Figure 7:
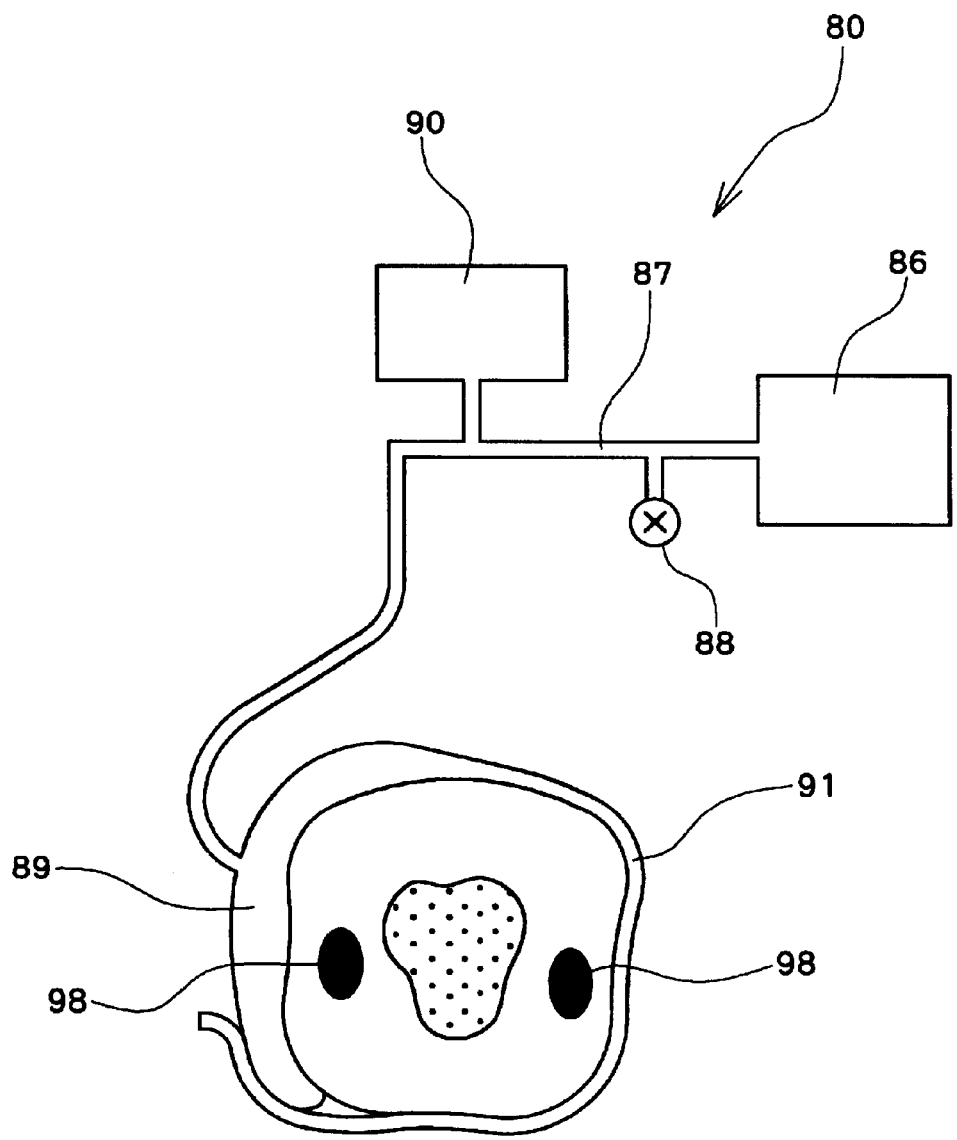
FIG. 7 is a view schematically showing a state in which a blood pressure is measured by a blood pressure measurement section.
Figure 8:
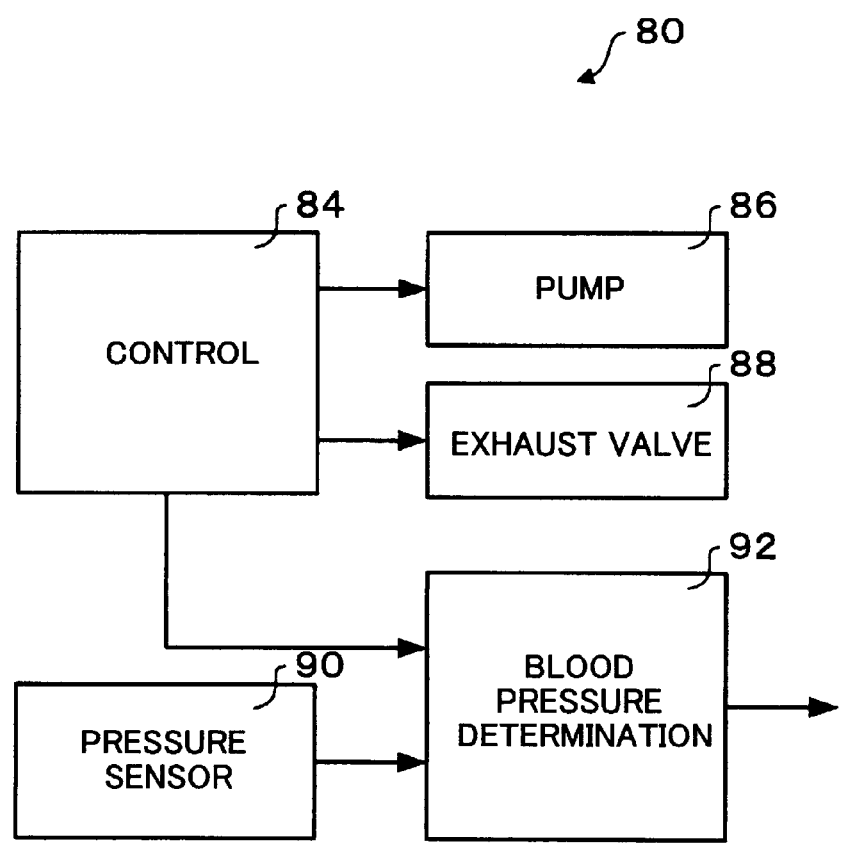
FIG. 8 is a block diagram showing the functional configuration of the blood pressure measurement section.

FIG. 7 shows an example of the blood pressure measurement section. FIG. 8 is a block diagram showing the functional configuration of the blood pressure measurement section 80 shown in FIG. 7. As shown in FIG. 7, the blood pressure measurement section 80 measures the blood pressure by means of a band 91 installed near the root of the finger, which is the area in which the pulse wave detection section 60 detects the pulse wave. The band 91 includes a pressure applying section 89 in the shape of a bag on the inner side thereof. The band 91 is wound around the finger so that the pressure applying section 89 is located at a position facing the digital artery 98.

The pressure applying section 89 is formed in the shape of a bag, to which a pump 86 and an exhaust valve 88 are connected through a tube 87. The volume of the pressure applying section 89 is controlled by adjusting the amount of fluid such as air, with which the pressure applying section 89 is filled, using the pump 86 and the exhaust valve 88. This enables controlling the pressure being applied to the digital artery 98 by the pressure applying section 89.

The tube 87 is equipped with a pressure sensor 90 which detects the pressure change of the fluid. The pressure sensor 90 is formed to detect the vibration of the pressure applying section 89 and the digital artery 98 transmitted as the pressure change of the fluid through the pressure applying section 89. Specifically, since the pressure applying section 89 located above the digital artery 98 is pressed corresponding to the vibration of the digital artery 98, the pressure of the fluid in the pressure applying section 89 is changed by the vibration of the digital artery 98. Therefore, the pressure sensor 90 which detects such a pressure change can output a signal corresponding to the vibration of the digital artery 98.

As shown in part of FIG. 8, the blood pressure measurement section 82 includes a control section 84 and a blood pressure determination section 92 in addition to each of the above-described sections.

The control section 84 adjusts the amount of fluid, with which the pressure applying section 89 is filled, by controlling the operation of the pump 86 and the exhaust valve 88. This causes the pressure applied by the pressure applying section 89 to be changed so that the pressure applying section 89 applies various levels of pressure within a predetermined range to the digital artery 98. The control section 84 includes a CPU and a memory in which a program for operating the CPU is stored, for example.

The blood pressure determination section 92 takes information on various levels of pressure being applied by the pressure applying section 89 from the control section 84, and determines maximum and minimum blood pressures based on a signal detected by the pressure sensor 90 at each pressure level. The blood pressure determination section 92 includes a CPU and a memory in which a program for operating the CPU is stored, for example.

The blood pressure measuring operation of the blood pressure measurement section 82 having the above-described configuration is described below.

The cuff-like band 91 is wound around the finger near the root of the finger so that the pressure applying section 89 is located at a position corresponding to the digital artery 98.

The control section 84 adjusts the amount of fluid, with which the pressure applying section 89 is filled, by controlling the pump 86 and the exhaust valve 88. This causes the pressure applied by the pressure applying section 89 to be changed so that the pressure applying section 89 applies various levels of pressure within a predetermined range to the digital artery 98. Specifically, the pressure applied by the pressure applying section 89 is controlled by the control section 84 within a range exceeding a commonly encountered blood pressure to some extent, such as 250 to 20 mmHg.

The pressure sensor 90, which detects the vibration of the digital artery 98, detects a signal corresponding to the vibration of the blood vessel wall due to blood flowing through the blood vessel constricted by the pressure applying section 89 at each pressure level applied by the pressure applying section 89. The results are stored in the blood pressure determination section 92 corresponding to each pressure level applied by the pressure applying section 89. Each pressure value applied by the pressure applying section 89 is transmitted to the blood pressure determination section 92 from the control section 84 which controls the pressure to be applied.

The blood pressure determination section 92 determines the blood pressure after a sufficient number of samples are obtained over the above-described pressure range of the pressure applying section 89. Specifically, the blood pressure determination section 92 determines the highest pressure applied by the pressure applying section 89 at which the pressure sensor 90 detects the vibration due to blood flowing through the constricted blood vessel as the maximum blood pressure. The blood pressure determination section 92 determines the lowest pressure applied by the pressure applying section 89 at which the pressure sensor 90 detects the vibration due to blood flowing through the constricted blood vessel as the minimum blood pressure. The principle of this blood pressure determination is the same as in a blood pressure measuring method which determines the blood pressure by monitoring the vibration of the blood vessel wall due to blood flowing through the blood vessel at the peripheral side of the artery constricted by the pressure applied by a brachium band while changing the pressure applied to the brachium band (auscultation method).

2.4 Operation of Central Blood Pressure Waveform Estimation Device

The central blood pressure waveform estimation device 70 of the present embodiment estimates and analyzes the central blood pressure waveform of the subject by operating in the same manner as the central blood pressure estimation device 10 of the first embodiment except that the blood pressure measuring operation is added and the following point differs.

Figure 14A:
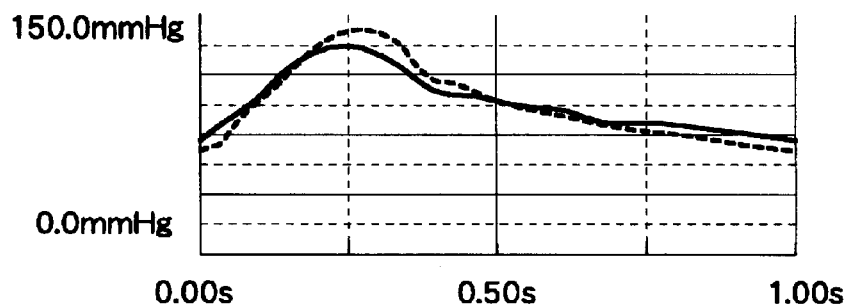
FIGS. 14A to 14C are waveform diagrams for describing the operation according to the second embodiment of the present invention.
Figure 14B:
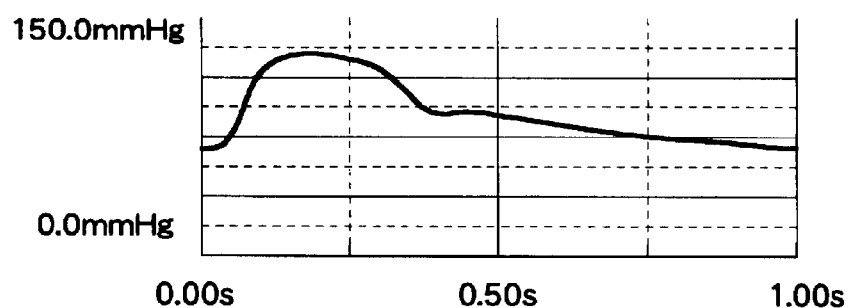

The operations of the present embodiment are described below with reference to FIGS. 14A to 14C. FIG. 14A shows aortic pressure waveforms before and after the administration of nitroglycerin. A broken line in FIG. 14A indicates the aortic pressure waveform before the administration of nitroglycerin to the subject. Generally, the blood pressure drops after the administration of nitroglycerin. In the present embodiment, the aortic pressure waveform of the subject after the administration of nitroglycerin is estimated (solid line in FIG. 14A).

Figure 14C:
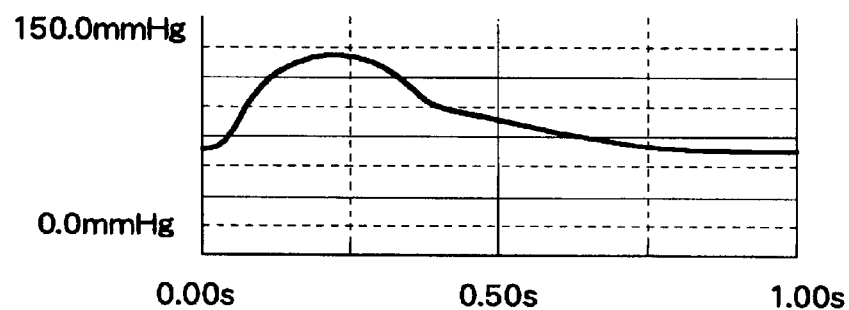

In the present embodiment, after the administration of nitroglycerin to the subject, the pulse waveform as the signal MH detected by the pulse wave detection section 60 in the same is that of a digital pulse wave as shown in FIG. 14C, for example. However, the pulse waveform is detected without accompanying the blood pressure value shown in FIG. 14C. The conversion section 72 converts the pulse waveform into the blood pressure waveform in the detection area using the blood pressure value measured by the blood pressure measurement section 80. FIG. 14B shows a radial artery pressure waveform measured by the blood pressure measurement section 80. It is unnecessary to measure the blood pressure each time the measurement is performed by storing in advance the above data in the blood pressure value storage section 100 shown in FIG. 13.

The conversion section 72 converts the pulse waveform into the corresponding blood pressure waveform based on the diastolic blood pressure (minimum blood pressure value) and the post-systolic blood pressure (maximum blood pressure value) measured by the blood pressure measurement section 80 shown in FIG. 6, or stored in the blood pressure value storage section 100 shown in FIG. 13, so that the pulse waveform has an amplitude of the minimum and maximum blood pressure values. This enables the digital pulse waveform accompanying the amplitude of the blood pressure value (blood pressure waveform) to be obtained, as shown in FIG. 14C.

When the blood pressure waveform obtained by calculation of the conversion section 72 (FIG. 14C) and the transfer function stored in the transfer function storage section 26 are input to the central blood pressure waveform calculation section 24, the central blood pressure waveform calculation section 24 calculates the central blood pressure waveform corresponding to the blood pressure waveform using the above data. The solid line shown in FIG. 14A indicates the calculated (estimated) central blood pressure waveform (aortic pressure waveform). As indicated by the solid line in FIG. 14A, the blood pressure drops in the aortic pressure waveform after the administration of nitroglycerin in comparison with the aortic pressure waveform before the administration of nitroglycerin indicated by the broken line in FIG. 14A. Therefore, the aortic pressure waveform which coincides with the fact can be estimated.

2.5 Effects of Second Embodiment

As described above, the central blood pressure waveform estimation device 70 according to the present embodiment is capable of deriving the central blood pressure waveform, specifically, the blood pressure waveform in the origin of the aorta using the peripheral blood pressure waveform obtained by converting the peripheral pulse waveform detected non-invasively.

3. Modifications 3.1 Each of the above-described embodiments illustrates an example in which the pulse wave detection section uses a sensor utilizing a light emitting device and a light receiving device. However, the pulse wave detection section may utilize a pressure sensor which is located above the peripheral artery such as the radial artery. In this case, the pulse wave (pressure pulse wave) is detected using applanation tonometry which measures the pressure using a pressure sensor pressed against the artery so that part of the blood vessel wall is flattened.

Figure 9:
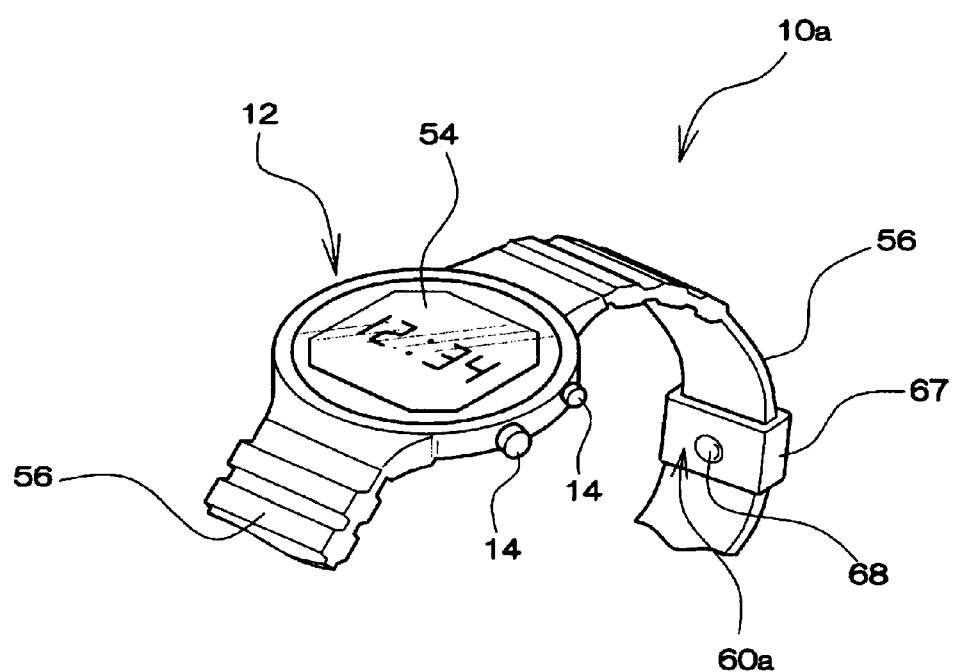
FIG. 9 is a perspective view of a central blood pressure waveform estimation device having the pulse wave detection section of a modification.
Figure 10:
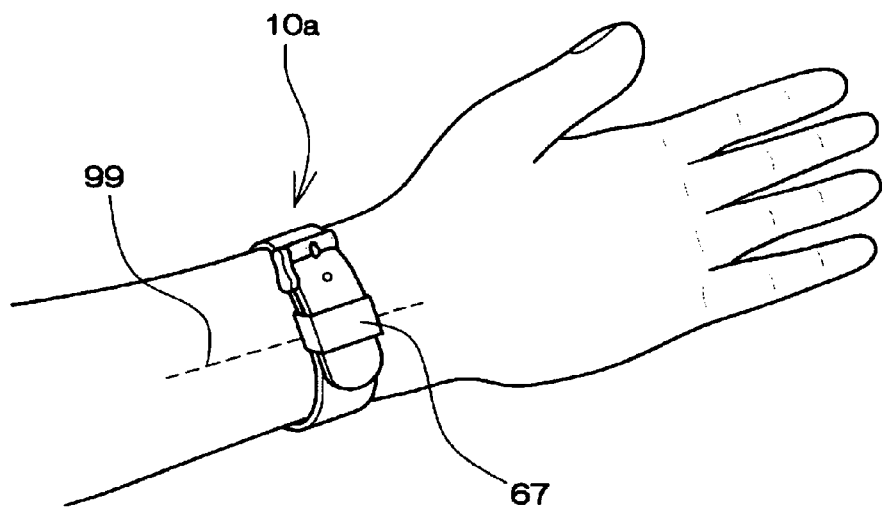
FIG. 10 is a perspective view of a hand and wrist wearing the central blood pressure waveform estimation device shown in FIG. 9.

FIGS. 9 and 10 are views showing a central blood pressure waveform estimation device 10a using such a pulse wave detection section. FIG. 9 is an oblique view showing the appearance of the central blood pressure waveform estimation device 10a. FIG. 10 is an oblique view showing a state in which the central blood pressure waveform estimation device 10a is wound around the wrist.

As shown in FIGS. 9 and 10, the central blood pressure waveform estimation device 10a includes a sensor holding section 67 provided at the wrist band 56 attached to the body 12 so as to be able to move along the wrist band 56. A pulse wave detection section 60a includes a pressure sensor 68 formed to project from the sensor holding section 67. The pulse wave detection section 60a and the body 12 are connected through wiring (not shown) such as an FPC (flexible printed circuit) substrate which transmits a signal detected by the pulse wave detection section 60a.

When using the central blood pressure waveform estimation device 10a, the central blood pressure waveform estimation device 10a is wound around the wrist of the subject so that the sensor holding section 67 is located near the radial artery 99, as shown in FIG. 10. The sensor holding section 67 is moved along the wrist band 56 so that the pulse wave detection section 60a provided on the sensor holding section 67 is located above the radial artery 99, for example.

When the pulse wave detection section 60a is appropriately pressed against the radial artery 99 of the subject, the pulse wave corresponding to the vibration of the blood vessel wall due to the change in the blood flow in the artery is transmitted to the pulse wave detection section 60a. This enables the central blood pressure waveform estimation device 10a to detect the pulse wave at any time. This pulse waveform is detected as a waveform having almost the same shape as the blood pressure waveform in the blood vessel.

Figure 11A:
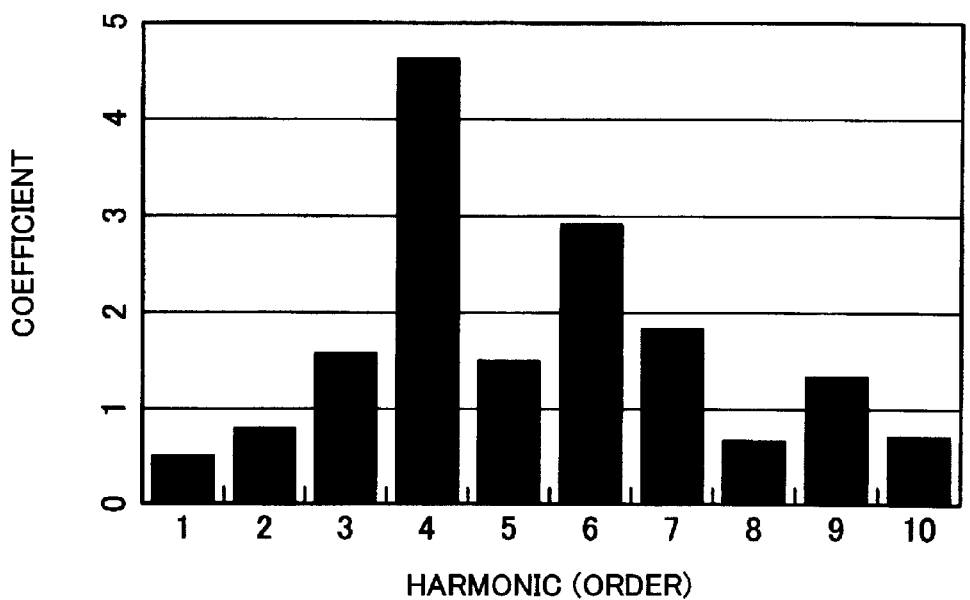
FIGS. 11A and 11B are bar charts of a coefficient and a phase for each harmonic, showing examples of a transfer function stored in the transfer function storage section of a modification.
Figure 11B:
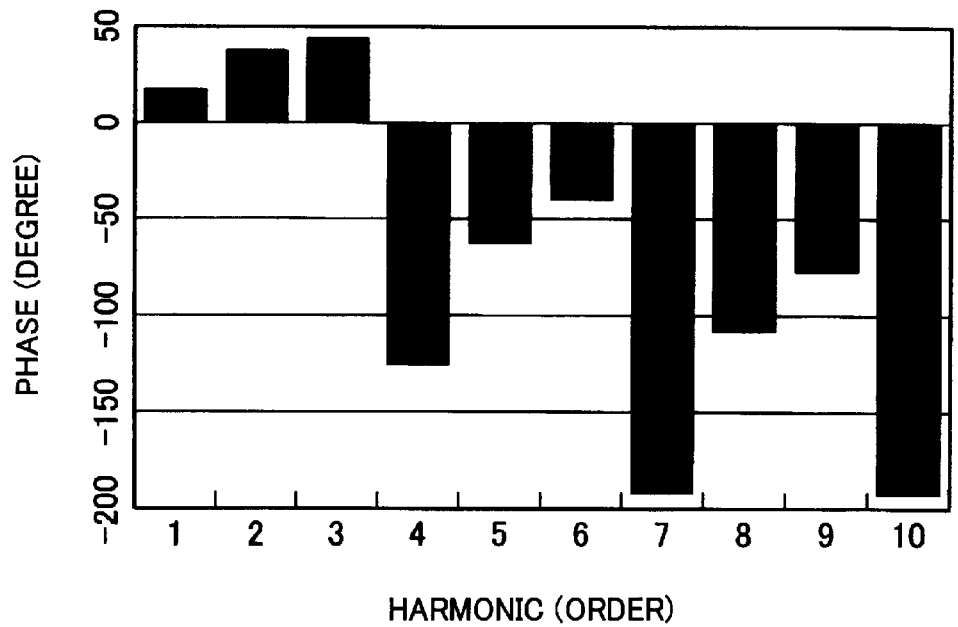

FIGS. 11A and 11B show examples of the calculation results for the transfer function of the pulse waveform detected in the radial artery for the central blood pressure waveform, specifically, the blood pressure waveform in the origin of the aorta as graphs of the coefficient and the phase for each harmonic. As shown in FIGS. 4A and 4B and FIGS. 11A and 11B, the transfer function calculated for the pulse waveform in the radial artery in this modification has almost the same features as the transfer function calculated for the pulse waveform (plethysmogram) obtained by detecting the change in the blood flow in the capillary plexus near the root of the finger using a photosensor in the first embodiment. In this modification, the transfer function is also stored in the transfer function storage section 26.

3.2 Each of the above-described embodiments illustrates an example in which the transfer function storage section 26 stores one transfer function calculated in advance based on the central blood pressure waveform, specifically, the blood pressure waveform in the origin of the aorta which is invasively measured in advance using a micro-manometer utilizing a catheter or the like, and the peripheral pulse waveform detected in advance by the pulse wave detection section 60 or the pulse wave detection section formed in the same manner as the pulse wave detection section 60.

However, the transfer function storage section 26 may store a plurality of transfer functions corresponding to various states of a subject. The term "various states of a subject" refers to states in which at least either the cardiac function state or the arterial state differs, such as a state after a meal, bath, or exercise. The transfer function storage section 26 may store a plurality of transfer functions corresponding to different frequencies of the pulse, for example. In this case, the central blood pressure waveform calculation section 24 may selectively use the transfer function corresponding to the pulse rate from a plurality of transfer functions based on information derived from the pulse wave detected by the pulse wave detection section 60, for example. This allows the central blood pressure waveform to be calculated using the transfer function corresponding to various states of the subject. Because of this, the central blood pressure waveform can be derived from the pulse wave in the peripheral artery with high precision regardless of the active state of the subject.

Similarly, the blood pressure value storage section 100 shown in FIG. 13 may store a plurality of blood pressure values corresponding to various states of the subject. This is because the blood pressure value varies depending upon various states in which at least either the cardiac function state or the arterial state of the subject differs, such as a state after a meal, bath or exercise. Therefore, the blood pressure value storage section 100 shown in FIG. 13 may store a plurality of blood pressure values corresponding to different pulse rates, for example. In this case, the conversion section 72 shown in FIG. 6 may selectively use the blood pressure value corresponding to the pulse rate from a plurality of blood pressure values based on information derived from the pulse wave detected by the pulse wave detection section 60, for example. This allows the central blood pressure waveform to be calculated using the blood pressure value corresponding to various states of the subject. An index which indicates the characteristics of the pulse waveform detected by the pulse wave detection section 60 (for example, the ratio of the pre-systolic wave height to the post-systolic wave height) may be used in place of the pulse rate. Alternatively, states of a subject at the time of measurement may be input from the data input section 42 shown in FIG. 13. As a state of a subject which may vary the blood pressure value, there are states after a meal, bath, exercise and the like, being different from the resting period, or a psychological tension state, or a psychological relaxation state. In addition to the blood pressure value during the resting period, a plurality of blood pressure values corresponding to the above-described states may be stored in the blood pressure value storage section 100. The blood pressure value selected from a plurality of blood pressure values based on information input from the data input section 42 may be read by the conversion section 72.

The transfer function storage section 26 may store a plurality of transfer functions corresponding to different ages. The central blood pressure waveform calculation section 24 may calculate the central blood pressure waveform by selectively using the transfer function corresponding to the age or the physiological age of the subject, whose pulse wave is detected by the pulse wave detection section 60, from a plurality of transfer functions. This enables the central blood pressure waveform to be calculated using the transfer function corresponding to the age or the physiological age of the subject, whereby the central blood pressure waveform can be derived from the pulse wave in the peripheral artery with high precision.

3.3 A modification provided with a change analysis section 39 described below is also possible. In this modification, the configuration and the operations are the same as those in the first embodiment except for the following point.

Figure 12:
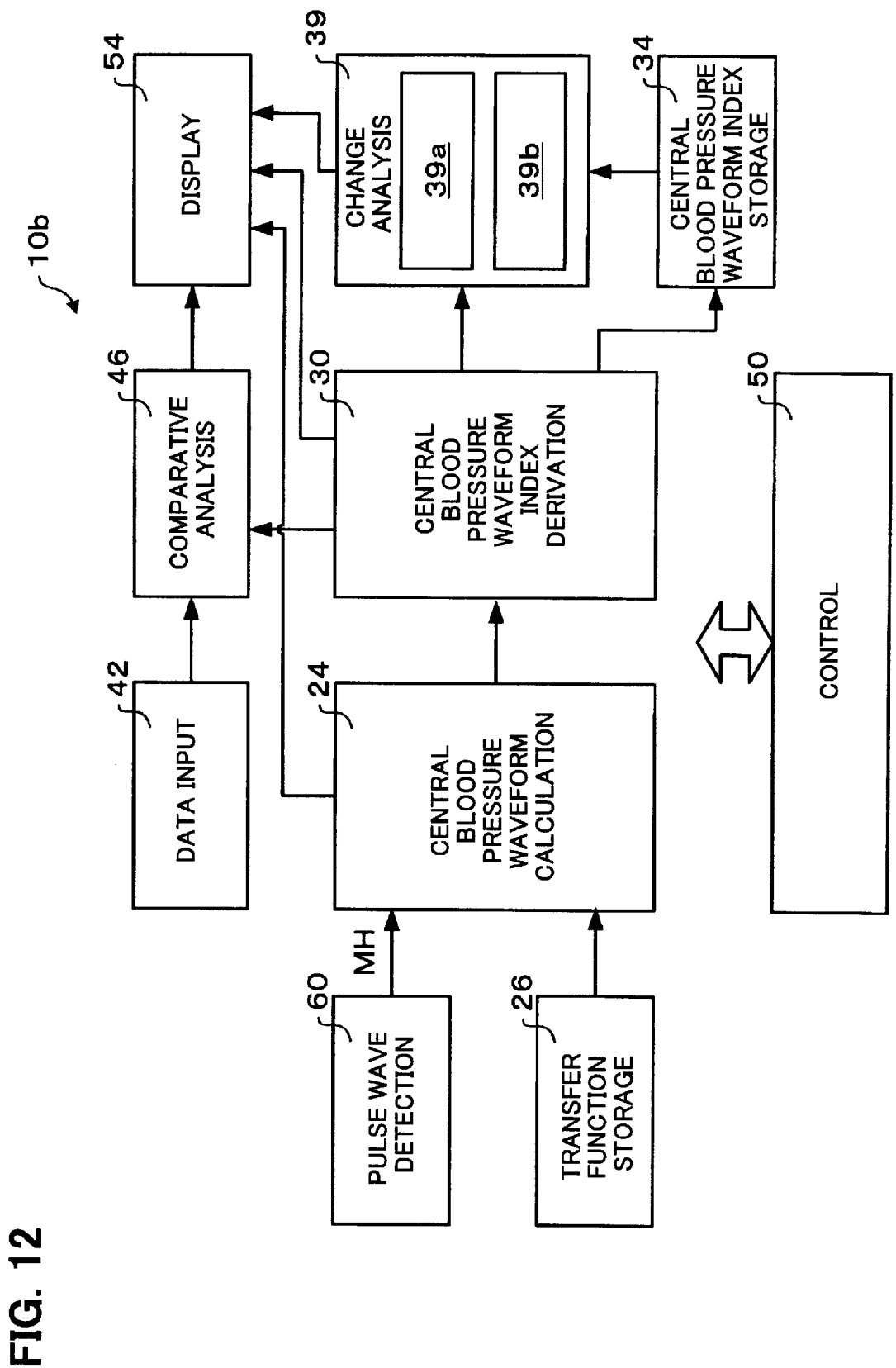
FIG. 12 is a block diagram showing the functional configuration of the central blood pressure waveform estimation device of a modification.

FIG. 12 is a block diagram showing the functional configuration of a central blood pressure waveform estimation device 75 of this modification. In the central blood pressure waveform estimation device 75, the change analysis section 39 includes a basal central blood pressure waveform index derivation section 39a and a basal central blood pressure waveform index storage section 39b.

The basal central blood pressure waveform index derivation section 39a derives the index of the central blood pressure waveform when the basal metabolism of the subject is in the lowest region in a predetermined period of time, such as in one day, based on the index stored in the central blood pressure waveform index storage section 34. The basal metabolism in humans generally reaches the lowest state (basal state) while sleeping from 2 AM to 4 AM in any day. The basal index is an index of the central blood pressure waveform in the basal state in any day, for example.

The basal central blood pressure waveform index derivation section 39a is not limited to one which derives the index of the central blood pressure waveform when the basal metabolism of the subject is in the lowest region in any day. For example, the basal central blood pressure waveform index derivation section 39a may derive the index of the central blood pressure waveform as the basal index when the basal metabolism of the subject is in the lowest region during a predetermined period of time such as one week, one month, three months, or one year.

The basal central blood pressure waveform index derivation section 39a may derive an index during resting obtained by providing measurement conditions such as after resting for five minutes during daily activities as the basal index.

The basal central blood pressure waveform index storage section 39b stores the basal index derived by the basal central blood pressure waveform index derivation section 39a.

The change analysis section 39 analyzes the change in the index based on the index derived by the central blood pressure waveform index derivation section 30 and the basal index stored in the basal central blood pressure waveform index storage section 39b, and outputs the analysis results to the display section 54.

The change analysis section 39 may store the basal index derived as the index of the central blood pressure waveform when the basal metabolism is in the lowest region during a period of time such as one day, one week, one month, three months, or one year, in the basal central blood pressure waveform index storage section 39b. The change analysis section 39 may compare this basal index with the basal index derived after a predetermined period of time, such as one month, six months, or one year, and output the comparison results to the display section 54.

The basal index derived by the basal central blood pressure waveform index derivation section 39a may be directly output to the display section 54 so that the display section 54 displays the basal index.

3.4 Each of the above-described embodiments illustrates the case where the area in which the pulse wave is detected by the pulse wave detection section is the root of the finger. However, the area in which the pulse wave is detected by the pulse wave detection section is not limited to the root of the finger insofar as the capillary plexus, in which a number of capillary vessels are distributed near the skin, is present in the area.

3.5 Each of the above-described embodiments illustrates an example in which the display section 54 including a display device such as a liquid crystal display device displays information, such as the index derived by the central blood pressure waveform index derivation section 30, analysis results by the comparative analysis section, analysis results by the change analysis section 38, or the central blood pressure waveform calculated by the central blood pressure waveform calculation section 24, specifically, the blood pressure waveform in the origin of the aorta, using characters, graphs, or the like. However, a display section including a printer, or a voice synthesizer and a speaker, may be used instead of the display section 54 or together with the display section 54. The display section may display or print out the information using characters or graphs, or report using voice output.

3.6 The present invention is not limited to the above-described embodiments, and various modifications can be made within the scope of the invention or equivalents of the claims.

What is claimed is:

1. A central blood pressure waveform estimation device comprising:
    a pulse wave detection section which non-invasively detects a peripheral pulse wave;
    a transfer function storage section which stores a transfer function calculated in advance based on a waveform of the peripheral pulse wave detected by the pulse wave detection section and a measured central blood pressure waveform corresponding to the peripheral pulse waveform; and
    a central blood pressure waveform calculation section which calculates a central blood pressure waveform corresponding to a waveform of a peripheral pulse wave newly detected by the pulse wave detection section, based on the newly-detected peripheral pulse waveform and the transfer function; and
    a central blood pressure waveform index derivation section which derives an index from a central blood pressure waveform calculated by the central blood pressure waveform calculation section.

2. The central blood pressure waveform estimation device as defined in claim 1,
    wherein the transfer function storage section stores a plurality of transfer functions corresponding to different physiological ages; and
    wherein the central blood pressure waveform calculation section calculates a central blood pressure waveform by selecting a transfer function corresponding to the physiological age of a subject whose pulse wave is detected by the pulse wave detection section, from the plurality of transfer functions.

3. The central blood pressure waveform estimation device as defined in claim 1,
    wherein the index derived by the central blood pressure waveform index derivation section is a pre-systolic blood pressure.

4. The central blood pressure waveform estimation device as defined in claim 1,
    wherein the index derived by the central blood pressure waveform index derivation section is a post-systolic blood pressure.

5. The central blood pressure waveform estimation device as defined in claim 1,
    wherein the index derived by the central blood pressure waveform index derivation section is a diastolic blood pressure.

6. The central blood pressure waveform estimation device as defined in claim 1,
    wherein the index derived by the central blood pressure waveform index derivation section is a differential pressure between a post-systolic blood pressure and a blood pressure at a dicrotic notch.

7. The central blood pressure waveform estimation device as defined in claim 1,
    wherein the index derived by the central blood pressure waveform index derivation section is a ratio of a post-systolic blood pressure to a blood pressure at the peak of a tidal wave.

8. The central blood pressure waveform estimation device as defined in claim 1, further comprising:
    a central blood pressure waveform index storage section which stores the index of a central blood pressure waveform; and
    a change analysis section which analyzes the change in the index of a central blood pressure waveform, based on an index newly derived by the central blood pressure waveform index derivation section and the index of the central blood pressure waveform stored in the central blood pressure waveform index storage section.

9. The central blood pressure waveform estimation device as defined in claim 8,
    wherein the change analysis section includes:
        a basal central blood pressure waveform index derivation section which derives an index of a basal central blood pressure waveform, which is an index of a central blood pressure waveform when basal metabolism of a subject is in the lowest region in a predetermined period of time, from the index of the central blood pressure waveform stored in the central blood pressure waveform index storage section; and
        a basal central blood pressure waveform index storage section which stores the basal central blood pressure waveform index derived by the basal central blood pressure waveform index derivation section, and
        wherein the change in the index of a central blood pressure waveform is analyzed, based on the index of the central blood pressure waveform derived by the central blood pressure waveform index derivation section and the basal central blood pressure waveform index stored in the basal central blood pressure waveform index storage section.

10. The central blood pressure waveform estimation device as defined in claim 1, further comprising:
    a data input section to which an actual age of a subject is input; and
    a comparative analysis section which compares and analyzes an index of a central blood pressure waveform, based on the index of the central blood pressure waveform derived by the central blood pressure waveform index derivation section and a standard index of a central blood pressure waveform at the actual age.

11. The central blood pressure waveform estimation device as defined in claim 1,
    wherein the pulse wave detection section is formed to detect a plethysmogram which changes corresponding to the blood flow, as the change in the amount of erythrocytes in capillary vessels near the skin.

12. The central blood pressure waveform estimation device as defined in claim 1,
wherein the transfer function storage section stores a plurality of transfer functions corresponding to a plurality of different states of a single subject.

13. The central blood pressure waveform estimation device as defined in claim 12,
wherein the central blood pressure waveform calculation section calculates a central blood pressure waveform by selecting one transfer function from the plurality of transfer functions based on information detected by the pulse wave detection section.

14. The central blood pressure waveform estimation device as defined in claim 1,
wherein the transfer function storage section stores a plurality of transfer functions corresponding to different ages; and
wherein the central blood pressure waveform calculation section calculates a central blood pressure waveform by selecting a transfer function corresponding to the age of a subject whose pulse wave is detected by the pulse wave detection section, from the plurality of transfer functions.

15. A peripheral blood pressure waveform detection device comprising:
a pulse wave detection section which non-invasively detects a peripheral pulse wave;
a blood pressure value storage section which stores a value of a blood pressure measured previously in an area near a portion in which a peripheral pulse wave is detected by the pulse wave detection section;
a conversion section which converts a waveform of the peripheral pulse wave detected by the pulse wave detection section into a peripheral blood pressure waveform using the blood pressure value stored in the blood pressure value storage section; and
wherein the blood pressure value storage section stores a plurality of blood pressure values corresponding to a plurality of different states of a single subject.

16. The peripheral blood pressure waveform detection device as defined in claim 15,
wherein the pulse wave detected by the pulse wave detection section is a plethysmogram which changes corresponding to the blood flow.

17. The peripheral blood pressure waveform detection device as defined in claim 15,
wherein the conversion section reads a blood pressure value selected from the plurality of blood pressure values stored in the blood pressure value storage section, based on information from the pulse wave detection section.

18. The peripheral blood pressure waveform detection device as defined in claim 15, further comprising:
an input section to which a state of a subject is input,
wherein the conversion section reads a blood pressure value selected from the plurality of blood pressure values stored in the blood pressure value storage section, based on information from the input section.

19. A central blood pressure waveform estimation device comprising:
a pulse wave detection section which non-invasively detects a peripheral pulse wave;
a transfer function storage section which stores a transfer function calculated in advance based on a waveform of the peripheral pulse wave detected previously and a measured central blood pressure waveform corresponding to the peripheral pulse waveform;
a central blood pressure waveform calculation section which calculates a central blood pressure waveform corresponding to a waveform of a peripheral pulse wave newly detected by the pulse wave detection section, based on the newly-detected peripheral pulse waveform and the transfer function; and
a central blood pressure waveform index derivation section which derives an index from a central blood pressure waveform calculated by the central blood pressure waveform calculation section.

20. The central blood pressure waveform estimation device as defined in claim 19, further comprising:
a data input section to which the actual age of a subject is input; and
a comparative analysis section which compares and analyzes an index of a central blood pressure waveform, based on the index of the central blood pressure waveform derived by the central blood pressure waveform index derivation section and a standard index of a central blood pressure waveform at the actual age.

21. The central blood pressure waveform estimation device as defined in claim 19,
wherein the pulse wave detection section is formed to detect a plethysmogram which changes corresponding to the blood flow, as the change in the amount of erythrocytes in capillary vessels near the skin.

22. The central blood pressure waveform estimation device as defined in claim 19,
wherein the transfer function storage section stores a plurality of transfer functions corresponding to a plurality of different states of a single subject.

23. The central blood pressure waveform estimation device as defined in claim 22,
wherein the central blood pressure waveform calculation section calculates a central blood pressure waveform by selecting one transfer function from the plurality of transfer functions based on information detected by the pulse wave detection section.

24. The central blood pressure waveform estimation device as defined in claim 19,
wherein the transfer function storage section stores a plurality of transfer functions corresponding to different ages; and
wherein the central blood pressure waveform calculation section calculates a central blood pressure waveform by selecting a transfer function corresponding to the age of a subject whose pulse wave is detected by the pulse wave detection section, from the plurality of transfer functions.

25. The central blood pressure waveform estimation device as defined in claim 19,
wherein the transfer function storage section stores a plurality of transfer functions corresponding to different physiological ages; and
wherein the central blood pressure waveform calculation section calculates a central blood pressure waveform by selecting a transfer function corresponding to the physiological age of a subject whose pulse wave is detected by the pulse wave detection section, from the plurality of transfer functions.

26. The central blood pressure waveform estimation device as defined in claim 19, further comprising:
a central blood pressure waveform index storage section which stores the index of the central blood pressure waveform; and
a change analysis section which analyzes the change in the index of the central blood pressure waveform, based on an index newly derived by the central blood pressure waveform index derivation section and the index of the central blood pressure waveform stored in the central blood pressure waveform index storage section.

27. The central blood pressure waveform estimation device as defined in claim 26,
wherein the change analysis section includes:
a basal central blood pressure waveform index derivation section which derives an index of the basal central blood pressure waveform, which is an index of the central blood pressure waveform when basal metabolism of a subject is in the lowest region in a predetermined period of time, from the index of the central blood pressure waveform stored in the central blood pressure waveform index storage section; and
a basal central blood pressure waveform index storage section which stores the basal central blood pressure waveform index derived by the basal central blood pressure waveform index derivation section, and
wherein the change in the index of a central blood pressure waveform is analyzed, based on the index of the central blood pressure waveform derived by the central blood pressure waveform index derivation section and the basal central blood pressure waveform index stored in the basal central blood pressure waveform index storage section.

28. A central blood pressure waveform estimation device comprising:
a pulse wave detection section which non-invasively detects a peripheral pulse wave;
a blood pressure measurement section which measures a blood pressure in an area near a portion in which a peripheral pulse wave is detected by the pulse wave detection section;
a conversion section which converts a waveform of the peripheral pulse wave detected by the pulse wave detection section into a peripheral blood pressure waveform using a value of the blood pressure measured by the blood pressure measurement section;
a transfer function storage section which stores a transfer function calculated in advance based on the peripheral blood pressure waveform obtained by the conversion section and a measured central blood pressure waveform corresponding to the peripheral blood pressure waveform;
a central blood pressure waveform calculation section which calculates a central blood pressure waveform corresponding to a peripheral blood pressure waveform obtained by converting a waveform of a pulse wave newly detected by the pulse wave detection section using the conversion section, based on the peripheral blood pressure waveform and the transfer function; and
a central blood pressure waveform index derivation section which derives an index from a central blood pressure waveform calculated by the central blood pressure waveform calculation section.

29. The central blood pressure waveform estimation device as defined in claim 28, further comprising:
a central blood pressure waveform index storage section which stores the index of the central blood pressure waveform; and
a change analysis section which analyzes the change in the index of the central blood pressure waveform, based on an index newly derived by the central blood pressure waveform index derivation section and the index of the central blood pressure waveform stored in the central blood pressure waveform index storage section.

30. The central blood pressure waveform estimation device as defined in claim 29,
wherein the change analysis section includes:
a basal central blood pressure waveform index derivation section which derives an index of the basal central blood pressure waveform, which is an index of the central blood pressure waveform when basal metabolism of a subject is in the lowest region in a predetermined period of time, from the index of the central blood pressure waveform stored in the central blood pressure waveform index storage section; and
a basal central blood pressure waveform index storage section which stores the basal central blood pressure waveform index derived by the basal central blood pressure waveform index derivation section, and
wherein the change in the index of a central blood pressure waveform is analyzed, based on the index of the central blood pressure waveform derived by the central blood pressure waveform index derivation section and the basal central blood pressure waveform index stored in the basal central blood pressure waveform index storage section.

31. The central blood pressure waveform estimation device as defined in claim 28,
wherein the pulse wave detection section is formed to detect a plethysmogram which changes corresponding to the blood flow, as the change in the amount of erythrocytes in capillary vessels near the skin.

32. The central blood pressure waveform estimation device as defined in claim 28,
wherein the transfer function storage section stores a plurality of transfer functions corresponding to a plurality of different states of a single subject.

33. The central blood pressure waveform estimation device as defined in claim 32,
wherein the central blood pressure waveform calculation section calculates a central blood pressure waveform by selecting one transfer function from the plurality of transfer functions based on information detected by the pulse wave detection section.

34. The central blood pressure waveform estimation device as defined in claim 28,
wherein the transfer function storage section stores a plurality of transfer functions corresponding to different ages; and
wherein the central blood pressure waveform calculation section calculates a central blood pressure waveform by selecting a transfer function corresponding to the age of a subject whose pulse wave is detected by the pulse wave detection section, from the plurality of transfer functions.

35. The central blood pressure waveform estimation device as defined in claim 28,
wherein the transfer function storage section stores a plurality of transfer functions corresponding to different physiological ages; and
wherein the central blood pressure waveform calculation section calculates a central blood pressure waveform by selecting a transfer function corresponding to the physiological age of a subject whose pulse wave is detected by the pulse wave detection section, from the plurality of transfer functions.

36. The central blood pressure waveform estimation device as defined in claim 28, further comprising:
a data input section to which the actual age of a subject is input; and
a comparative analysis section which compares and analyzes an index of a central blood pressure waveform, based on the index of the central blood pressure waveform derived by the central blood pressure waveform index derivation section and a standard index of a central blood pressure waveform at the actual age.

37. A central blood pressure waveform estimation device comprising:
- a pulse wave detection section which non-invasively detects a peripheral pulse wave;
- a blood pressure value storage section which stores a value of a blood pressure measured previously in an area near a portion in which a peripheral pulse wave is detected by the pulse wave detection section;
- a conversion section which converts a waveform of the peripheral pulse wave detected by the pulse wave detection section into a peripheral blood pressure waveform using the blood pressure value stored in the blood pressure value storage section;
- a transfer function storage section which stores a transfer function calculated in advance based on the peripheral blood pressure waveform obtained by the conversion section and a measured central blood pressure waveform corresponding to the peripheral blood pressure waveform;
- a central blood pressure waveform calculation section which calculates a central blood pressure waveform corresponding to a peripheral blood pressure waveform obtained by converting a waveform of a pulse wave newly detected by the pulse wave detection section using the conversion section, based on the peripheral blood pressure waveform and the transfer function; and
- a central blood pressure waveform index derivation section which derives an index from a central blood pressure waveform calculated by the central blood pressure waveform calculation section.

38. The central blood pressure waveform estimation device as defined in claim 37, further comprising:
- a central blood pressure waveform index storage section which stores the index of the central blood pressure waveform; and
- a change analysis section which analyzes the change in the index of the central blood pressure waveform, based on an index newly derived by the central blood pressure waveform index derivation section and the index of the central blood pressure waveform stored in the central blood pressure waveform index storage section.

39. The central blood pressure waveform estimation device as defined in claim 38,
wherein the change analysis section includes:
- a basal central blood pressure waveform index derivation section which derives an index of the basal central blood pressure waveform, which is an index of the central blood pressure waveform when basal metabolism of a subject is in the lowest region in a predetermined period of time, from the index of the central blood pressure waveform stored in the central blood pressure waveform index storage section; and
- a basal central blood pressure waveform index storage section which stores the basal central blood pressure waveform index derived by the basal central blood pressure waveform index derivation section, and
- wherein the change in the index of a central blood pressure waveform is analyzed, based on the index of the central blood pressure waveform derived by the central blood pressure waveform index derivation section and the basal central blood pressure waveform index stored in the basal central blood pressure waveform index storage section.

40. The central blood pressure waveform estimation device as defined in claim 37, further comprising:
- a data input section to which the actual age of a subject is input; and
- a comparative analysis section which compares and analyzes an index of a central blood pressure waveform, based on the index of the central blood pressure waveform derived by the central blood pressure waveform index derivation section and a standard index of a central blood pressure waveform at the actual age.

41. The central blood pressure waveform estimation device as defined in claim 37,
wherein the pulse wave detection section is formed to detect a plethysmogram which changes corresponding to the blood flow, as the change in the amount of erythrocytes in capillary vessels near the skin.

42. The central blood pressure waveform estimation device as defined in claim 37,
wherein the transfer function storage section stores a plurality of transfer functions corresponding to a plurality of different states of a single subject.

43. The central blood pressure waveform estimation device as defined in claim 42,
wherein the central blood pressure waveform calculation section calculates a central blood pressure waveform by selecting one transfer function from the plurality of transfer functions based on information detected by the pulse wave detection section.

44. The central blood pressure waveform estimation device as defined in claim 42,
wherein the blood pressure value storage section stores a plurality of blood pressure values corresponding to a plurality of different states of a single subject.

45. The central blood pressure waveform estimation device as defined in claim 44,
wherein the conversion section reads a blood pressure value selected from the plurality of blood pressure values stored in the blood pressure value storage section, based on information from the pulse wave detection section.

46. The central blood pressure waveform estimation device as defined in claim 44, further comprising:
- an input section to which a state of a subject is input,
- wherein the conversion section reads a blood pressure value selected from the plurality of blood pressure values stored in the blood pressure value storage section, based on information from the input section.

47. The central blood pressure waveform estimation device as defined in claim 37,
wherein the transfer function storage section stores a plurality of transfer functions corresponding to different ages; and
wherein the central blood pressure waveform calculation section calculates a central blood pressure waveform by selecting a transfer function corresponding to the age of a subject whose pulse wave is detected by the pulse wave detection section, from the plurality of transfer functions.

48. The central blood pressure waveform estimation device as defined in claim 37,
wherein the transfer function storage section stores a plurality of transfer functions corresponding to different physiological ages; and
wherein the central blood pressure waveform calculation section calculates a central blood pressure waveform by selecting a transfer function corresponding to the physiological age of a subject whose pulse wave is detected by the pulse wave detection section, from the plurality of transfer functions.

* * * * *